United States Patent [19]

Brändström et al.

[11] Patent Number: 5,039,806
[45] Date of Patent: Aug. 13, 1991

[54] NOVEL PHARMACOLOGICALLY ACTIVE COMPOUND PYRIDYL METHYLSULFINYL BENZIMIDAZOLE

[75] Inventors: Arne E. Brändström, Göteborg; Stig A. I. Carlsson, Mölnlycke; Britt I. M. Källsson, Mölndal; Per L. Lindberg, Askim, all of Sweden

[73] Assignee: AB Hassle, Molndal, Sweden

[21] Appl. No.: 408,719

[22] Filed: Sep. 18, 1989

Related U.S. Application Data

[60] Division of Ser. No. 379,703, Jul. 12, 1989, abandoned, which is a continuation of Ser. No. 266,330, Nov. 1, 1988, abandoned, which is a continuation of Ser. No. 21,992, Mar. 5, 1987, abandoned, which is a continuation-in-part of Ser. No. 884,863, Jul. 16, 1986, abandoned, which is a continuation of Ser. No. 578,418, Feb. 9, 1984, abandoned.

[30] Foreign Application Priority Data

Feb. 11, 1983 [SE] Sweden .............................. 83007369

[51] Int. Cl.$^5$ .............................................. C07D 401/12
[52] U.S. Cl. ................................................. 546/271
[58] Field of Search .......................... 546/271; 514/338

[56] References Cited

U.S. PATENT DOCUMENTS

| | | | |
|---|---|---|---|
| 4,045,563 | 8/1977 | Berntsson et al. | 546/271 |
| 4,045,564 | 8/1977 | Berntsson et al. | 546/271 |
| 4,337,257 | 6/1982 | Janggren et al. | 546/271 |
| 4,359,465 | 11/1982 | Ruwart | 546/271 |
| 4,472,409 | 9/1984 | Senn-Bilfinger | 546/271 |
| 4,727,150 | 2/1988 | Nohara et al. | 546/271 |

FOREIGN PATENT DOCUMENTS

| | | |
|---|---|---|
| 0005129 | 4/1981 | European Pat. Off. |
| 0074341 | 3/1983 | European Pat. Off. |
| 2134523 | 8/1984 | United Kingdom |

OTHER PUBLICATIONS

Brandstrom et al., Scand. J. Gastroenterol 20 (Suppl. 108), 15–22, 1985.

Primary Examiner—Jane T. Fan
Attorney, Agent, or Firm—White & Case

[57] ABSTRACT

Novel compounds of the formula

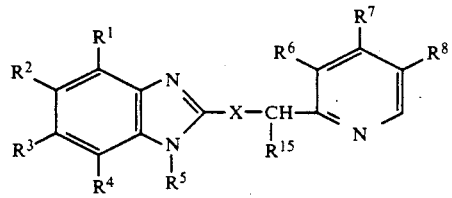

pharmaceutical compositions containing such compounds as active ingredient, and the use of the compounds in medicine.

1 Claim, No Drawings

NOVEL PHARMACOLOGICALLY ACTIVE COMPOUND PYRIDYL METHYLSULFINYL BENZIMIDAZOLE

This application is a division of application Ser. No. 379,703, filed on July 12, 1989 now abandoned which is a continuation of Ser. No. 07/266,330 filed Nov. 1, 1988, now abandoned, which is a continuation of 07/021,992 filed Mar. 5, 1987, now abandoned, which is a cip of 06/884,863 filed July 16, 1986, now abandoned, which is a continuation of 06/578,418 filed Feb. 9, 1984, now abandoned.

DESCRIPTION

1. Field of the Invention

The object of the present invention is to provide novel compounds, and therapeutically acceptable salts thereof, which inhibit exogenously or endogenously stimulated gastric acid secretion and provide gastrointestinal cytoprotective effects and thus can be used in the prevention and treatment of peptic ulcer.

The present invention relates to the use of the compounds of the invention or therapeutically acceptable salts thereof, for inhibiting gastric acid secretion as well as providing gastrointestinal cytoprotective effects in mammals and man. In a more general sense, the compounds of the invention may be used for prevention and treatment of gastrointestinal inflammatory diseases in mammals and man, including e.g. gastritis, gastric ulcer and duodenal ulcer. Furthermore, the compounds may be used for prevention and treatment of other gastrointestinal disorders, where cytoprotective and/or gastric antisecretory effect is desirable e.g. in patients with gastrinomas, in patients with acute upper gastrointestinal bleeding, and in patients with a history of chronic and excessive ethanol consumption. The invention also relates to pharmaceutical compositions containing at least one compound of the invention, or a therapeutically acceptable salt thereof, as active ingredient. In a further aspect, the invention relates to processes for preparation of such new compounds and to novel intermediates in the preparation of the compounds of the invention.

2. Prior Art

Benzimidazole derivatives intended for inhibiting gastric acid secretion are disclosed in the British patent specifications 1 500 043 and 1 525 958, in the U.S. Pat. No. 4 182 766, in the European patent specification 0 005 129, and in the Belgian patent specification 890 024. Benzimidazole derivatives proposed for use in the treatment or prevention of special gastrointestinal inflammatory disease are disclosed in the European patent application with publication No. 0 045 200.

THE INVENTION

It has been found that the compounds of the formula

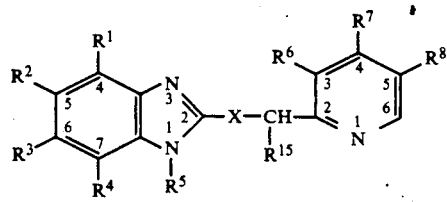

wherein
X is —S— or

$R^{15}$ is H, $CH_3$ or $C_2H_5$;
$R^1$, $R^2$, $R^3$ and $R^4$, which are the same or different, are
(a) H
(b) halogen
(c) —CN
(d) —CHO
(e) —$CF_3$
(f)

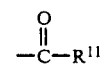

(g)

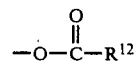

(h) —$CH(OR^{13})_2$
(i) —$(Z)_n$—A—D
(j) aryl
(k) aryloxy
(l) alkylthio containing 1-6 carbon atoms
(m) —$NO_2$
(n) alkylsulfinyl containing 1-6 carbon atoms or wherein
(o) adjacent groups $R^1$, $R^2$, $R^3$ and $R^4$ together with the adjacent carbon atoms in the benzimidazole ring form a 5-, 6- or 7-membered monocyclic ring or a 9-, 10- or 11-membered bicyclic ring which rings may be saturated or unsaturated and may contain 0–3 hetero atoms selected from N and O, and which rings may be optionally substituted with 1–4 substituents selected from alkyl groups with 1–3 carbon atoms, alkylene radicals containing 4–5 carbon atoms giving spiro compounds, or two or four of these substituents together form one or two oxo groups

Whereby if $R^1$, $R^2$, $R^3$ and $R^4$ together with the adjacent carbon atoms in the benzimidazole ring form two rings they may be condensed with each other, in which formulas $R^{11}$ and $R^{12}$, which are the same or different, are
(a) aryl,
(b) alkoxy containing 1-4 carbon atoms,
(c) alkoxyalkoxy containing 1-3 carbon atoms in each alkoxy part,
(d) arylalkoxy containing 1-2 carbon atoms in the alkoxy part,
(e) aryloxy,
(f) dialkylamino containing 1-3 carbon atoms in the alkyl parts, or (g) pyrrolidino or piperidino, optionally substituted with alkyl containing 1-3 carbon atoms:

$R^{13}$ is
(a) alkyl containing 1-4 carbon atoms, or
(b) alkylene containing 2-3 carbon atoms;

Z is —O— or

n is 0 or 1;

A is
(a) alkylene containing 1-6 carbon atoms
(b) cycloalkylene containing 3-6 carbon atoms
(c) alkenylene containing 2-6 carbon atoms
(d) cycloalkenylene containing 3-6 carbon atoms, or
(e) alkynylene containing 2-6 carbon atoms;

Q is
(a) —CN
(b)

(c)

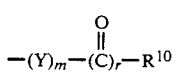

wherein
$R^9$ is
(a) alkoxy containing 1-5 carbon atoms, or
(b) dialkylamino containing 1-3 carbon atoms in the alkyl parts;

m is 0 or 1;
r is 0 or 1;

Y is
(a) —O—
(b) —NH—
(c) —$NR^{10}$—;

$R^{10}$ is
(a) H
(b) alkyl containing 1-3 carbon atoms,
(c) arylalkyl containing 1-2 carbon atoms in the alkyl part, or
(d) aryl;

$R^5$ is
(a) H or
(b)

wherein
$R^{14}$ is
(a) alkyl containing 1-6 carbon atoms,
(b) arylalkyl containing 1-2 carbon atoms in the alkyl part
(c) aryl
(d) alkoxy containing 1-4 carbon atoms
(e) arylalkoxy containing 1-2 carbon atoms in the alkyl part
(f) aryloxy
(g) amino (h) mono- or dialkylamino containing 1-4 carbon atoms in the alkyl part(s)
(i) arylalkylamino containing 1-2 carbon atoms in the alkyl part
(j) arylamino;

$R^6$ and $R^8$, which are the same or different, are
(a) H or
(b) alkyl containing 1-5 carbon atoms;

$R^7$ is
(a) H
(b) alkyl containing 1-8 carbon atoms
(c) alkoxy containing 1-8 carbon atoms
(d) alkenyloxy containing 2-5 carbon atoms
(e) alkynyloxy containing 2-5 carbon atoms
(f) alkoxyalkoxy containing 1-2 carbon atoms in each alkoxy group
(g) dialkylaminoalkoxy containing 1-2 carbon atoms in the alkyl substituents on the amino nitrogen and 1-4 carbon atoms in the alkoxy group
(h) oxacycloalkyl containing one oxygen atom and 3-7 carbon atoms
(i) oxacycloalkoxy containing two oxygen atoms and 4-7 carbon atoms
(j) oxacycloalkylalkyl containing one oxygen atom and 4-7 carbon atoms
(k) oxacycloalkylalkoxy containing two oxygen atoms and 4-6 carbon atoms, or
(l) $R^6$ and $R^7$, or $R^7$ and $R^8$ together with the adjacent carbon atoms in the pyridine ring form a ring wherein the part constituted by $R^6$ and $R^7$, or $R^7$ and $R^8$, is —CH=CH—CH=CH
—O—$(CH_2)_p$—
—$CH_2(CH_2)_p$—
—O—CH=CH—
—NH—CH=CH—

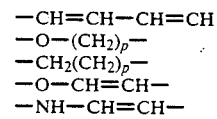

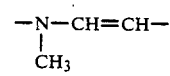

wherein p is 2, 3 or 4 and the O and N atoms always are attached to position 4 in the pyridine ring;

and physiologically acceptable salts of the compounds I wherein X is S;

with the provisos that
(a) not more than one of $R^6$, $R^7$ and $R^8$ is hydrogen,
(b) when X is SO, $R^5$ is H and $R^6$, $R^7$ and $R^8$ are selected only from hydrogen, methyl, methoxy, ethoxy, methoxyethoxy and ethoxyethoxy and at the same time more than one of $R^1$, $R^2$ $R^3$ and $R^4$ are hydrogen, then $R^1$, $R^2$, $R^3$ and $R^4$ cannot be selected only from alkyl groups, halogen, alkoxycarbonyl, alkoxy or alkanoyl,
(c) when X is S, $R^5$ is H, alkanoyl or alkoxycarbonyl, and $R^6$, $R^7$ and $R^8$ are selected only from hydrogen, methyl, ethyl, methoxy, ethoxy, methoxyethoxy and ethoxyethoxy and at the same time more than one of $R^1$, $R^2$, $R^3$ and $R^4$ are hydrogen, then $R^1$, $R^2$, $R^3$ and $R^4$ cannot be selected only from alkyl groups, halogen, alkoxycarbonyl, alkoxy, alkanoyl, trifluormethyl, or $NO_2$,
(d) when X is SO, one of $R^6$, $R^7$ and $R^8$ is H and the other two of $R^6$, $R^7$ and $R^8$ are alkyl, and at the same time more than one of $R^1$, $R^2$, $R^3$ and $R^4$ are hydrogen, then those radicals $R^1$, $R^2$, $R^3$ and $R^4$ which are not H cannot be selected only from alkyl, halogen, cyano, $$\overset{O}{\underset{\|}{-C}}\text{-(alkoxy), (alkyl)-}\overset{O}{\underset{\|}{OC}}\text{-(alkyl)-,}$$

alkoxy, hydroxyalkyl, CF$_3$, or $$\text{(alkyl)-}\overset{O}{\underset{\|}{C}}-,$$

(e) when R$^3$, R$^4$, R$^5$ and R$^{15}$ are H and simultaneously R$^6$ and R$^8$ are H or CH$_3$ and R$^7$ is OCH$_3$, then R$^1$ is not CF$_3$ when R$^2$ is H, and R$^2$ is not CF$_3$ when R$^1$ is H, are effective as gastrointestinal cytoprotectives and as inhibitors of gastric acid secretion in mammals and man as stated above.

Illustrative examples of the various radicals in the formula I are as follows. These illustrative examples will be applicable to different radicals depending on the number of carbon atoms prescribed for each radical. It will be understood that the expressions "alkyl" and "alkoxy" include straight, branched and cyclic structures.

Halogen: F, Cl, Br, I

Alkyl: CH$_3$, C$_2$H$_5$, n-C$_3$H$_7$, i-C$_3$H$_7$, n-C$_4$H$_9$, sec.-C$_4$H$_9$, iso.-C$_4$H$_9$, tert.-C$_4$H$_9$, n-C$_5$H$_{11}$, n-C$_6$H$_{13}$,

[cyclic alkyl structures]

Alkylene: —CH$_2$—, —CH$_2$CH$_2$—, —(CH$_2$)$_3$—, —CH$_2$—CH—,
$\qquad\qquad\qquad\qquad\qquad\qquad\qquad\qquad\qquad\quad |$
$\qquad\qquad\qquad\qquad\qquad\qquad\qquad\qquad\qquad\text{CH}_3$

—(CH$_2$)$_4$—, —(CH$_2$)$_5$—, —(CH$_2$)$_6$—

Cycloalkylene: [cyclic structures]

Alkenylene: —CH=CH—, —CH$_2$—CH=CH—,
—CH$_2$—CH=CH—CH$_2$—,
—(CH$_2$)$_2$—CH=CH—CH$_2$—,
—(CH$_2$)$_3$—CH=CH—CH$_2$—

Alkylthio: —S—CH$_3$, —S—C$_2$H$_5$, —S-i-C$_3$H$_7$

Cycloalkenylene: [cyclic structures]

Alkynylene: —C≡C—, —CH$_2$—C≡C—,

Alkoxy: —OCH$_3$, —OC$_2$H$_5$, —O-n-C$_3$H$_7$, —O-i-C$_3$H$_7$,
—O-n-C$_4$H$_9$, —O-iso-C$_4$H$_9$, —O-sec.-C$_4$H$_9$,
—O-tert.-C$_4$H$_9$, —O-n-C$_5$H$_{11}$,

[cyclic alkoxy structures]

Alkoxyalkoxy: —OCH$_2$OCH$_3$, —OCH$_2$CH$_2$OCH$_3$,
—OCH$_2$CH$_2$OCH$_2$CH$_3$,
—OCH$_2$CH$_2$CH$_2$OCH$_2$CH$_2$CH$_3$ Aryl: [phenyl]

Arylalkoxy: —OCH$_2$—[phenyl], —OCH$_2$CH$_2$—[phenyl]

Aryloxy: —O—[phenyl]

Arylalkyl: —CH$_2$—[phenyl], —(CH$_2$)$_2$—[phenyl], $\qquad\overset{\text{CH}_3}{\underset{|}{-\text{CH}}}$—[phenyl]

Alkenyloxy: —O—CH=CH$_2$, —O—CH=CH—CH$_3$,
—O—CH=CH—C$_2$H$_5$,
—O—CH$_2$—CH=CH—CH$_2$CH$_3$ Alkynyloxy: —O—C≡CH, —O—CH$_2$—C≡CH,
—O—CH$_2$—C≡C—CH$_3$
—O—CH$_2$—C≡C—CH$_2$CH$_3$ Illustrative examples of the radical —CH(OR$^{13}$)$_2$ are:

[acetal structures with OCH$_3$, OC$_2$H$_5$, OCH$_2$CH$_2$CH$_3$ and cyclic O—CH$_2$ dioxolane/dioxane structures]

Illustrative examples of the ring structures involving R$^1$, R$^2$, R$^3$ or R$^4$ are

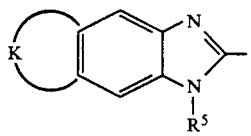

where K is

—CH₂CH₂CH₂—
—CH₂CH₂CH₂CH₂—
—CH₂—C(CH₃)₂—CH₂—
—(CH₂)₅—
—CH=CH—CH=CH—

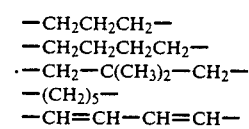

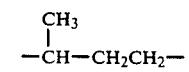

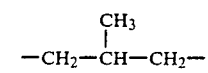

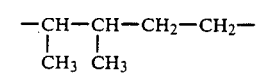

—(CH₂)₂—NH—
—CCH₂O—
—OCH₂CH₂O—
—O—C(CH₃)₂—O—
—O(CH₂)₃O—

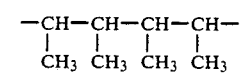

—O—C—O—

—CH₂—O—(CH₂)₂—O—

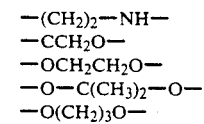

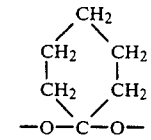

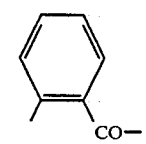

The radical —(Z)ₙ—A—D comprises the following radicals. The expression (alkyl 1-3c) etc. means alkyl groups containing 1, 2 or 3 carbon atoms.

A—CN $$A-\overset{O}{\underset{\|}{C}}-O-(alkyl\ 1\text{-}5c)$$

$$A-\overset{O}{\underset{\|}{C}}-N\begin{matrix}(alkyl\ 1\text{-}3c)\\(alkyl\ 1\text{-}3c)\end{matrix}$$

A—H

A—(alkyl 1-3c)

A—(alkyl 1-2c)—aryl

A—aryl

A—O—H

A—O—(alkyl 1-3c)

A—O—(alkyl 1-2c)—aryl

A—O—aryl

A—NH—H

A—NH—(alkyl 1-3c)

A—NH—(alkyl 1-2c)—aryl

A—NH—aryl $$A-\overset{R^{10}}{\underset{|}{N}}-H$$

$$A-\overset{R^{10}}{\underset{|}{N}}-(alkyl\ 1\text{-}3c)$$

$$A-\overset{R^{10}}{\underset{|}{N}}-(alkyl\ 1\text{-}2c)-aryl$$

$$A-\overset{R^{10}}{\underset{|}{N}}-aryl$$

$$A-O-\overset{O}{\underset{\|}{C}}-H$$

$$A-O-\overset{O}{\underset{\|}{C}}-(alkyl\ 1\text{-}3c)$$

$$A-O-\overset{O}{\underset{\|}{C}}-(alkyl\ 1\text{-}2c)-aryl$$

$$A-O-\overset{O}{\underset{\|}{C}}-aryl$$

$$A-NH-\overset{O}{\underset{\|}{C}}-H$$

$$A-NH-\overset{O}{\underset{\|}{C}}-(alkyl\ 1\text{-}3c)$$

$$A-NH-\overset{O}{\underset{\|}{C}}-(alkyl\ 1\text{-}2c)-aryl$$

A—NH—aryl $$A-\overset{R^{10}}{\underset{|}{N}}-\overset{O}{\underset{\|}{C}}-H$$

$$A-\overset{R^{10}}{\underset{|}{N}}-\overset{O}{\underset{\|}{C}}-(alkyl\ 1\text{-}3c)$$

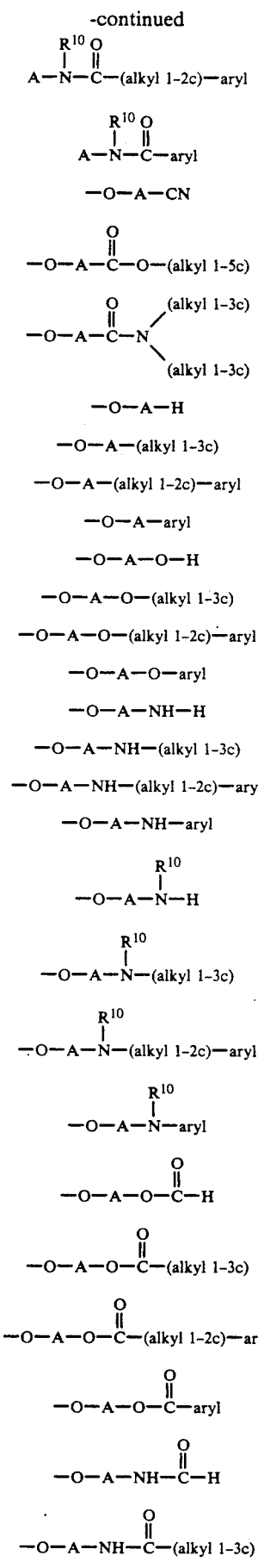
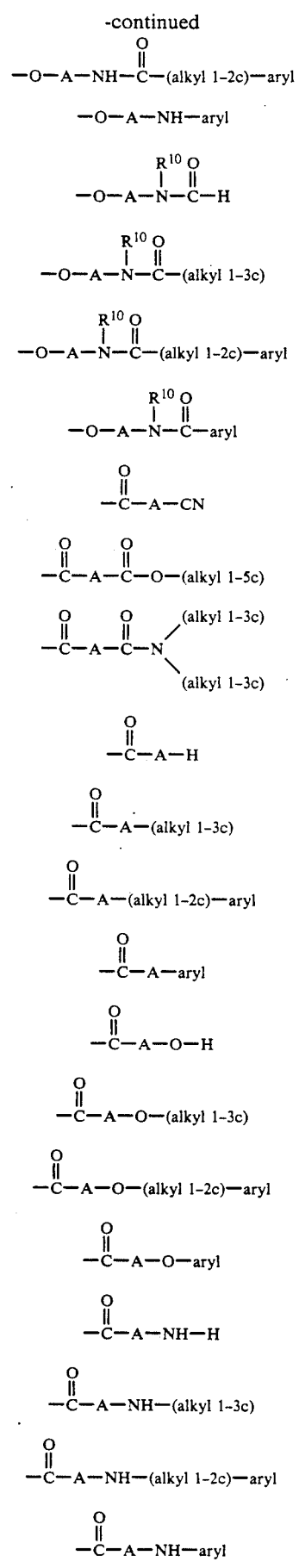

-continued
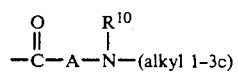
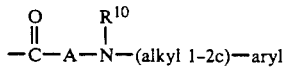
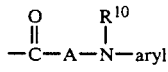
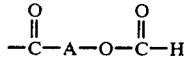
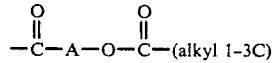
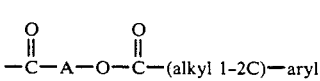
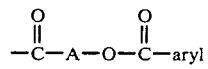
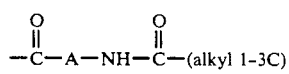
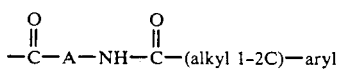
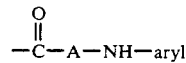
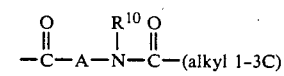
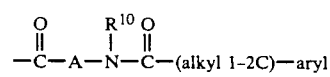
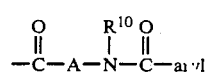
The radical
comprises the following radicals.
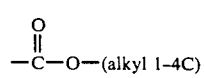
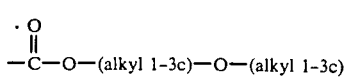
-continued
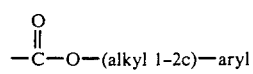
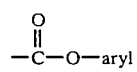
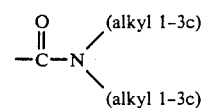
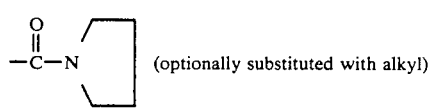 (optionally substituted with alkyl)
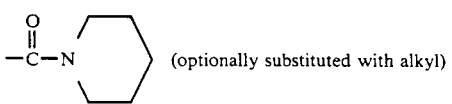 (optionally substituted with alkyl)
The radical
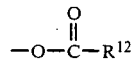
comprises the following radicals.
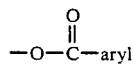
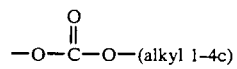
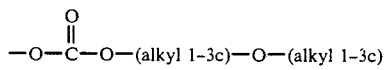
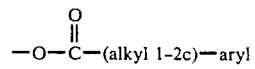
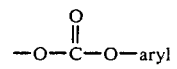
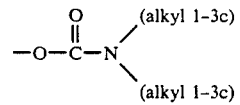
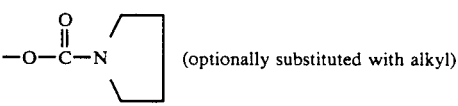 (optionally substituted with alkyl)
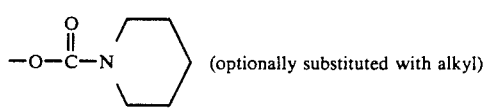 (optionally substituted with alkyl)
The radical
comprises the following radicals:

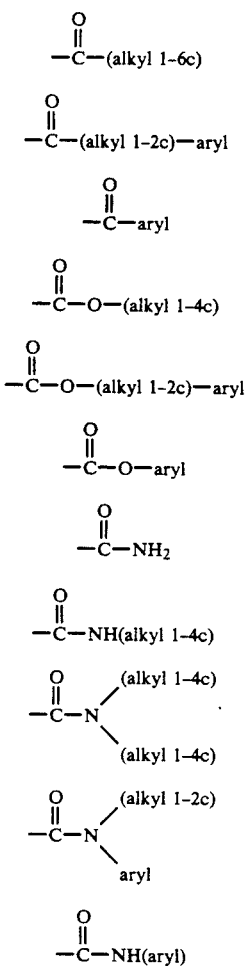

Further illustrative examples of the radicals in the formula I are:

alkylsulfinyl: SOCH$_3$, SOC$_2$H$_5$, SOCH$_2$CH$_2$CH$_3$, SO-i-C$_3$H$_7$, SO-n-C$_4$H$_9$, SO-n-C$_5$H$_{11}$

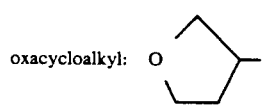

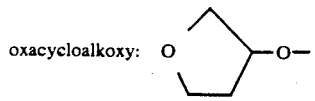

-continued

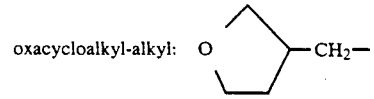

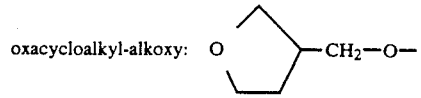

The compounds of the invention that are sulfoxides (X=SO) have an asymmetric centre in the sulfur atom, i.e. these compounds exist as two optical isomers (enantiomers), or if they also contain one or more asymmetric carbon atoms the compounds have two or more diastereomeric forms, each existing in two enantiomeric forms. Such asymmetric carbon atoms may be the carbon atom on which R$^{15}$ is attached (when R$^{15}$ is other than H) or a carbon atom in some of the substituents.

Both the pure enantiomers, racemic mixtures (50% of each enantiomer) and unequal mixtures of the two are within the scope of the present invention. It should be understood that all the diastereomeric forms possible (pure enantioners or racemic mixtures) are witin the scope of the invention.

The compounds of the invention that are sulfides (X=S) may be asymmetric due to one or more asymmetric carbon atoms, as described above. The different diastereomeric forms possible as well as the pure enantiomers and racemic mixtures are within the scope of the invention.

It should be noted that for all the compounds of the invention wherein R$^5$ is H the substituents R$^1$ and R$^4$ as well as R$^2$ and R$^3$ are considered to be equivalent. This is due to the tautomerism in the imidazole part of the benzimidazole nucleus causing an equilibrium between the two possible >NH—forms. This is illustrated by the following example:

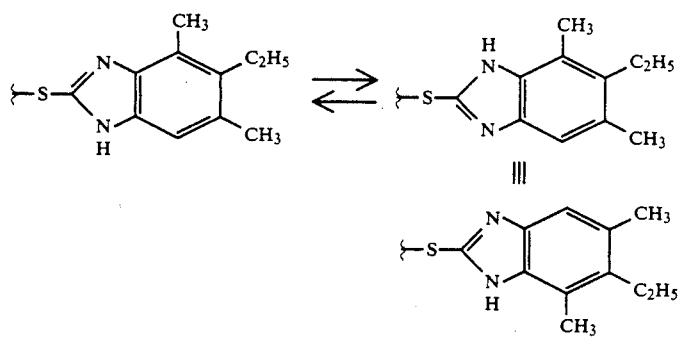

I. Preferred groups of the radicals R$^1$, R$^2$, R$^3$ and R$^4$ are:
1. H
2. halogens F, Cl, Br and the groups CN, CHO, CO(aryl), COO(alkyl), CF$_3$. SCH$_3$, SOCH$_3$ and NO$_2$
3. the groups alkylene-D, O-alkylene-D and CO-alkylene-D wherein D is CN, COO(alkyl), COR$^{10}$, OR$^{10}$ or R$^{10}$
4. aryl and aryloxy
5.

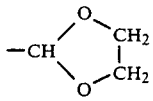

6. —CH$_2$CH$_2$CH$_2$—, —CH$_2$CH$_2$CH$_2$CH$_2$— and —CH=CH—CH=CH—
7.

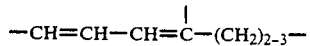

8. saturated heterocyclic ring structures having 2 oxygen atoms
9. unsaturated 6-membered heterocyclic ring structures having one nitrogen atom II. Further preferred groups of the radicals R$^1$, R$^2$, R$^3$ and R$^4$ are:
1. H
2. halogens Cl and Br and the groups CO(phenyl), COOCH$_3$, CF$_3$, SCH$_3$ and SOCH$_3$
3. the groups alkyl, alkoxyalkyl, aryloxyalkyl, arylalkyl, aryl
4. the groups alkoxy, alkoxyalkoxy, aryloxyalkoxy, arylalkoxy, aryloxy
5. the group alkanoyl
6. —CH$_2$CH$_2$CH$_2$—, —CH$_2$CH$_2$CH$_2$CH$_2$— and —CH=CH—CH=CH—
7.

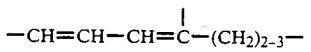

8. saturated heterocyclic ring structures having 2 oxygen atoms in 4,5-, 5,6- or 6,7- "catechol positions", e.g. (5,6-position shown)

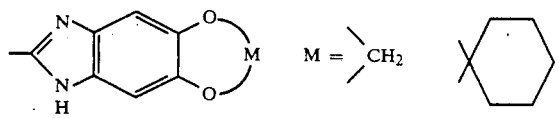

III. Still further preferred groups of the radicals R$^1$, R$^2$, R$^3$ and R$^4$ are:
1. H
2. Br and the groups COOCH$_3$ and CF$_3$
3. the groups CH$_3$, C$_2$H$_5$, CH(CH$_3$)$_2$, CH$_3$OCH$_2$CH$_2$—, phenyl
4. the groups CH$_3$O, CH$_3$(CH$_2$)$_6$O—, CH$_3$OCH$_2$CH$_2$O—, (phenyl)OCH$_2$CH$_2$CH$_2$O—, (phenyl)CH$_2$CH$_2$O—, (phenyl)O—
5. the groups CH$_3$CO—, C$_2$H$_5$CO—
6. —CH$_2$CH$_2$CH$_2$—, —CH$_2$CH$_2$CH$_2$CH$_2$—
7. —OCH$_2$O—,

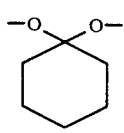

in the 5,6-"catechol position"

IV. Particularly preferred groups of the radicals R$^1$, R$^2$, R$^3$ and R$^4$ are: H, COOCH$_3$, CF$_3$, CH$_3$, C$_2$H$_5$, CH(CH$_3$)$_2$, CH$_3$O, —CH$_2$CH$_2$CH$_2$—, —CH$_2$CH$_2$CH$_2$CH$_2$— and —OCH$_2$O—

V. In a preferred embodiment, at least three of the radicals R$^1$, R$^2$, R$^3$ and R$^4$ are other than hydrogen, or they form at least one ring.

VI. In another preferred embodiment the radicals R$^1$ and R$^2$ form a ring structure VII. In another preferred embodiment the radicals R$^2$ and R$^3$ form a ring structure.

VIII. In a preferred embodiment at least three of the radicals R$^1$, R$^2$, R$^3$ and R$^4$ are other than hydrogen.

IX. In a preferred embodiment the radicals R$^1$, R$^2$, R$^3$ and R$^4$ are selected from H, halogen, CF$_3$, alkyl and alkoxy groups.

X. In a preferred embodiment the radicals R$^1$, R$^2$, R$^3$ and R$^4$ are selected from H, alkyl and alkoxy groups.

XI. In a preferred embodiment the radicals R$^1$, R$^2$, R$^3$ and R$^4$ are selected from H and alkyl groups.

XII. The preferred group of X is S.
XIII. The preferred group of X is SO.
XIV. The preferred group of R$^{15}$ is H.
XV. Preferred groups of the radical R$^5$ are H, arylcarbonyl, alkoxycarbonyl, arylalkoxycarbonyl, dialkylaminocarbonyl and arylaminocarbonyl.
XVI. Further preferred groups of the radical R$^5$ are H, phenylcarbonyl, methoxycarbonyl, tert-butoxycarbonyl, benzyloxycarbonyl, dimethylaminocarbonyl and phenylaminocarbonyl.
XVII. Particularly preferred of the radical R$^5$ is H.
XVIII. Preferred groups of the radicals R$^6$ and R$^8$ are:
1. H, CH$_3$, C$_2$H$_5$, C$_3$H$_7$ and CH(CH$_3$)$_2$
2. ring structures connecting position 4 in the pyridine ring.
XIX. Particularly preferred groups of the radicals R$^6$ and R$^8$ are H, CH$_3$, C$_2$H$_5$ and ring structures also connecting position 4 in the pyridine ring
XX. Preferred groups of the radical R$^7$ are:
1. H, CH$_3$, C$_2$H$_5$
2. OCH$_3$, OC$_2$H$_5$, OCH$_2$CH$_2$CH$_3$, O(CH$_2$)$_3$CH$_3$,

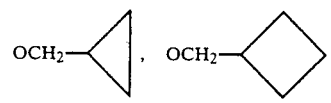

3. OCH$_2$CH=CH$_2$, OCH$_2$C≡CH
4. OCH$_2$CH$_2$OCH$_3$,

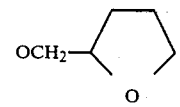

5. OCH$_2$CH$_2$N(CH$_3$)$_2$
6. —CH=CH—CH=CH—bound to positions 3 and 4, —CH=CH—CH=CH—bound to positions 4 and 5, —CH$_2$CH$_2$CH$_2$—bound to positions 3 and 4, —CH$_2$CH$_2$CH$_2$—bound to positions 4 and 5, —CH$_2$CH$_2$CH$_2$CH$_2$—bound to positions 3 and 4, —CH$_2$CH$_2$CH$_2$CH$_2$—bound to positions 4 and 5, —OCH$_2$CH$_2$—bound to positions 3 and 4, —OCH$_2$CH$_2$—bound to positions 4 and 5, —OCH$_2$CH$_2$CH$_2$—bound to positions 3 and 4, —OCH$_2$CH$_2$CH$_2$—bound to positions 4 and 5, XXI. Further preferred groups of the radical R$^7$ are:
1. CH$_3$

2. OCH₃, OC₂H₅, OCH₂CH₂CH(CH₃)₂
3. OCH₂CH=CH₂
4. OCH₂CH₂OCH₃,

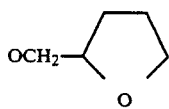

5. —CH₂CH₂CH₂—bound to positions 3 and 4,
—CH₂CH₂CH₂—bound to positions 4 and 5,
—CH₂CH₂CH₂CH₂—bound to positions 3 and 4,
—CH₂CH₂CH₂CH₂—bound to positions 4 and 5,
—OCH₂CH₂—bound to positions 3 and 4,
—OCH₂CH₂—bound to positions 4 and 5,
—OCH₂CH₂CH₂—bound to positions 3 and 4,
—OCH₂CH₂CH₂—bound to positions 4 and 5.

XXII. Particularly preferred groups of the radical R⁷ are CH₃, OCH₃, OCH₂CH₂CH(CH₃)₂,

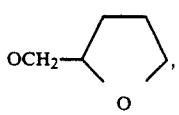

—OCH₂CH₂CH₂—bound to positions 3 and 4 or to positions 4 and 5.

XXIII. Preferred pyridyl substitution patterns are:

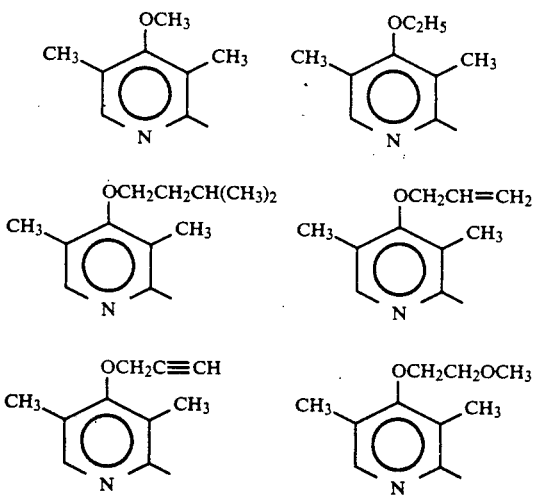

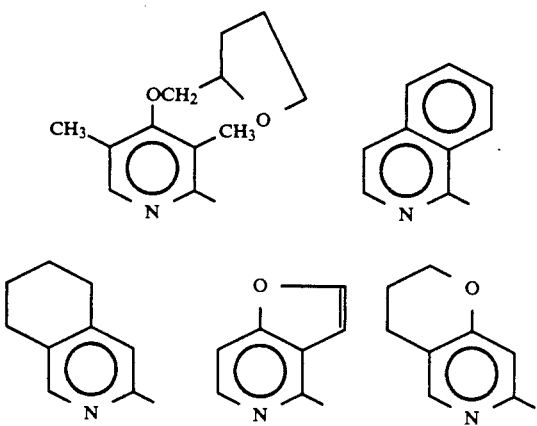

XXIV. Further preferred pyridyl substitution patterns are:

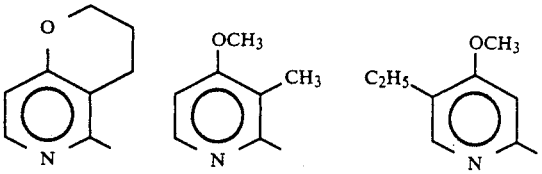

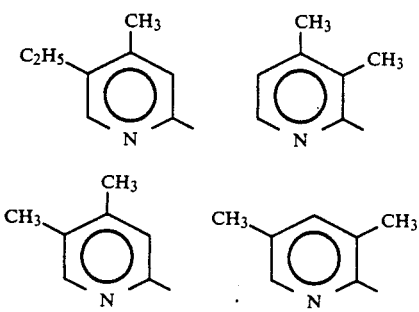

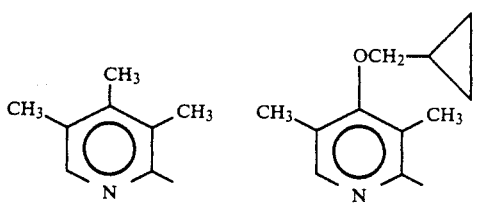

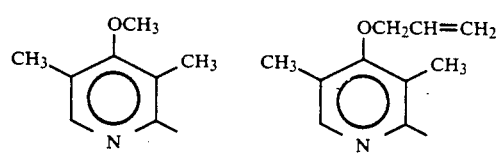

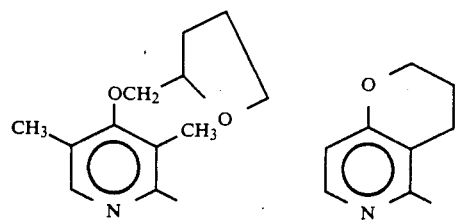

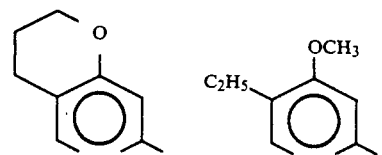

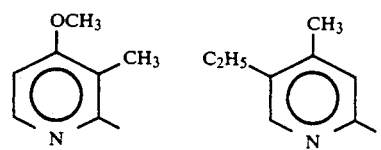

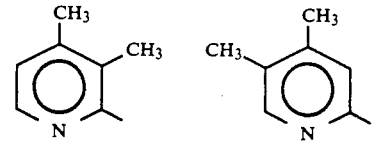

-continued

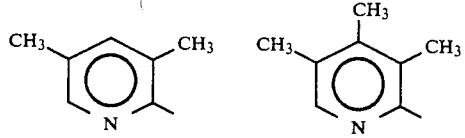

XXV. Still further preferred pyridyl substitution patterns are:

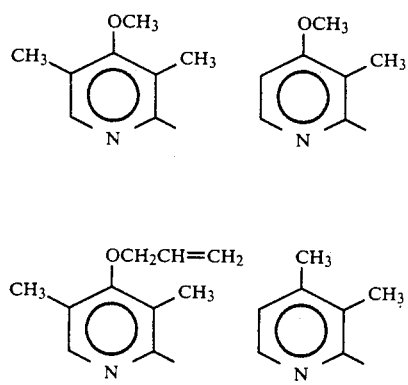

XXVI. Particularly preferred pyridyl substitution patterns are:

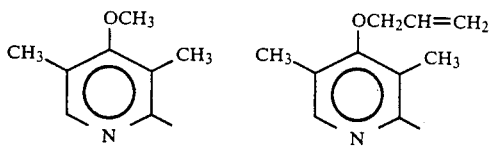

XXVII. In a preferred embodiment two of the radicals $R^6$, $R^7$ and $R^8$ form one ring structure and the third radical of $R^6$, $R^7$ and $R^8$ is H.

XXVIII. In a preferred embodiment $R^{15}$ and $R^5$ are H, at least three of the radicals $R^1$, $R^2$, $R^3$ and $R^4$ are other than H, $R^6$ and $R^8$ are H or $CH_3$ and $R^7$ is $CH_3$, $OCH_3$ or $OCH_2CH=CH_2$.

XXIX. In a preferred embodiment $R^{15}$ and $R^5$ are H, the radicals $R^1$, $R^2$, $R^3$ and $R^4$ form at least one ring structure, $R^6$ and $R^8$ are H or $CH_3$ and $R^7$ is $CH_3$, $OCH_3$ or $OCH_2CH=CH_2$.

XXX. Preferred compounds are those of the formula

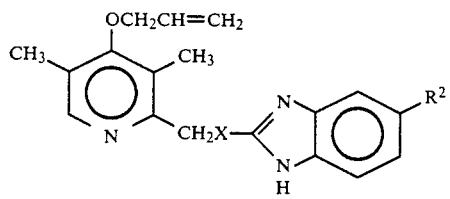

wherein $R^2$ is alkyl or alkoxy, preferably $CH_3$, $C_2H_5$, $CH(CH_3)_2$ and $OCH_3$, and X is S or SO.

Further illustrative examples of the radicals in the formula I are given in the examples and lists of specific compounds given elsewhere in this specification.

Illustrative examples of compounds included in the scope of the invention are given in the following Table 1.

TABLE 1

Illustrative examples of compounds included in the scope of the invention.

| X | R¹⁵ | R¹ | R² | R³ | R⁴ | R⁵ | R⁶ | R⁷ | R⁸ |
|---|---|---|---|---|---|---|---|---|---|
| S | H | CH₃ | CH₃ | CH₃ | CH₃ | H | CH₃ | OCH₂CH=CH₂ | CH₃ |
| SO | H | CH₃ | CH₃ | CH₃ | CH₃ | H | CH₃ | OCH₂CH=CH₂ | CH₃ |
| S | H | CH₃ | CH₃ | CH₃ | CH₃ | H | CH₃ | OCH₃ | CH₃ |
| SO | H | CH₃ | CH₃ | CH₃ | CH₃ | H | CH₃ | OCH₃ | CH₃ |
| S | H | CH₃ | CH₃ | CH₃ | H | H | CH₃ | OCH₂CH=CH₂ | CH₃ |
| SO | H | CH₃ | CH₃ | CH₃ | H | H | CH₃ | OCH₂CH=CH₂ | CH₃ |
| S | H | CH₃ | CH₃ | CH₃ | H | H | CH₃ | OCH₃ | CH₃ |
| SO | H | CH₃ | CH₃ | H | CH₃ | H | CH₃ | OCH₃ | CH₃ |
| S | H | CH₃ | CH₃ | H | CH₃ | H | CH₃ | OCH₂CH=CH₂ | CH₃ |
| SO | H | CH₃ | CH₃ | H | CH₃ | H | CH₃ | OCH₂CH=CH₂ | CH₃ |
| S | H | CH₃ | CH₃ | H | CH₃ | H | CH₃ | OCH₃ | CH₃ |
| SO | H | H | CH₃ | CH₃ | H | H | CH₃ | OCH₂CH=CH₂ | CH₃ |
| S | H | H | CH₃ | CH₃ | H | H | CH₃ | OCH₂CH=CH₂ | CH₃ |
| SO | H | CH₃ | CH₃ | H | H | H | CH₃ | OCH₃ | CH₃ |
| S | H | CH₃ | CH₃ | H | H | H | CH₃ | OCH₂CH=CH₂ | CH₃ |
| SO | H | H | H | H | CH₃ | H | CH₃ | OCH₂CH=CH₂ | CH₃ |
| S | H | H | OCH₃ | H | CH₃ | H | CH₃ | OCH₂CH=CH₂ | CH₃ |
| SO | H | H | OCH₃ | H | H | H | CH₃ | OCH₂CH=CH₂ | CH₃ |
| S | H | H | OCH₃ | H | H | H | CH₃ | OCH₃ | CH₃ |
| SO | H | H | OCH₃ | H | H | H | CH₃ | OCH₂CH=CH₂ | CH₃ |
| S | H | H | OCH₃ | H | H | H | CH₃ | OCH₂CH=CH₂ | CH₃ |
| SO | H | H | OCH₃ | H | H | H | CH₃ | OCH₂CH=CH₂ | CH₃ |
| S | H | H | OCH₃ | H | H | H | CH₃ | OCH₂C≡CH | CH₃ |
| SO | H | H | OCH₃ | H | H | H | CH₃ | OCH₂C≡CH | CH₃ |
| S | H | H | OCH₃ | H | H | H | CH₃ | OCH₂CH=CH₂ | CH₃ |
| SO | H | H | OCH₃ | H | H | H | CH₃ | O(CH₂)₃CH=CH₂ | CH₃ |
| S | H | H | OCH₃ | H | H | H | CH₃ | O(CH₂)₃CH₃ | CH₃ |
| SO | H | H | OCH₃ | H | H | H | CH₃ | OCH(CH₃)₂ | CH₃ |
| S | H | H | OCH₃ | H | H | H | CH₃ | OCH(CH₃)₂ | CH₃ |
| SO | H | H | OCH₃ | H | H | H | CH₃ | OC(CH₃)₃ | CH₃ |
| S | H | H | OCH₃ | H | H | H | CH₃ | OC(CH₃)₃ | CH₃ |
| S | H | H | OCH₃ | H | H | H | CH₃ | ⌬-O (cyclobutyloxy) | CH₃ |

TABLE 1-continued

Illustrative examples of compounds included in the scope of the invention.

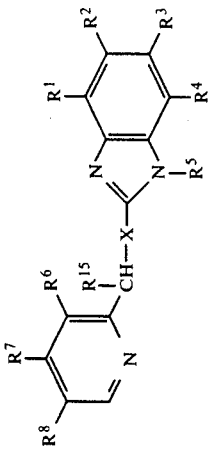

| X | $R^{15}$ | $R^1$ | $R^2$ | $R^3$ | $R^4$ | $R^5$ | $R^6$ | $R^7$ | $R^8$ |
|---|---|---|---|---|---|---|---|---|---|
| SO | H | H | $OCH_3$ | H | H | H | $CH_3$ | cyclobutyl-O- | $CH_3$ |
| S | H | H | $OCH_3$ | H | H | H | $CH_3$ | cyclopropyl-$CH_2$O- | $CH_3$ |
| SO | H | H | $OCH_3$ | H | H | H | $CH_3$ | cyclopropyl-$CH_2$O- | $CH_3$ |
| S | H | H | $OCH_3$ | H | H | H | $CH_3$ | cyclobutyl-$CH_2$O- | $CH_3$ |
| SO | H | H | $OCH_3$ | H | H | H | $CH_3$ | cyclobutyl-$CH_2$O- | $CH_3$ |
| S | H | H | $OCH_3$ | H | H | H | $CH_3$ | $O(CH_2)_2N(CH_3)_2$ | $CH_3$ |
| S | H | H | $OCH_3$ | H | H | H | $CH_3$ | $O(CH_2)_2N^{\oplus}H(CH_3)_2Cl^{\ominus}$ | $CH_3$ |
| SO | H | H | $OCH_3$ | H | H | H | $CH_3$ | $O(CH_2)_2N(CH_3)_2$ | $CH_3$ |
| S | H | H | $OCH_3$ | H | H | H | $CH_3$ | $OCH_2CH_2CH(CH_3)_2$ | $CH_3$ |
| SO | H | H | $OCH_3$ | H | H | H | $CH_3$ | $OCH_2CH_2CH(CH_3)_2$ | $CH_3$ |
| SO | H | H | $OCH_3$ | H | H | H | H | $OCH_3$ | $C_2H_5$ |
| S | H | H | $OCH_3$ | H | H | H | H | $O(CH_2)_3CH_3$ | $C_2H_5$ |
| SO | H | H | $OCH_3$ | H | H | H | H | $O(CH_2)_3CH_3$ | $C_2H_5$ |
| SO | H | H | $OCH_3$ | H | H | H | $CH_3$ | $OCH_2CH_2CH(CH_3)_2$ | $CH_3$ |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| SO | H | CH3 | OCH3 | CH3 | H | H | H | C2H5 | CH3 |
| SO | H | H | OCH3 | H | H | H | CH3 | OCH2CH2CH2-cyclopentyl | CH3 |
| SO | H | CH3 | OCH3 | CH3 | H | H | H | CH(CH3)2 | CH3 |
| S | H | H | OCH3 | H | H | H | H | —(CH2)4— | H |
| SO | H | H | OCH3 | H | H | H | H | —(CH2)4— | H |
| SO | H | H | OCH3 | H | H | H | H | —(CH2)3— | H |
| SO | H | H | OCH3 | H | H | H | H | —O—(CH2)3— | H |
| SO | H | H | OCH3 | H | H | H | H | —O—(CH2)2—O— | H |
| SO | H | S | OCH3 | H | H | H | H | —(CH2)2—O— | H |
| SO | H | H | OCH3 | H | H | H | H | —CH=CH—CH=CH— | H |
| SO | H | H | OCH3 | H | H | H | H | —CH=CH—CH=CH— | H |
| SO | H | H | OCH3 | H | H | H | H | —CH=CH—CH=CH— | H |
| S' | H | H | OCH3 | H | H | H | H | —CH=CH—CH=CH— | CH3 |
| SO | H | H | OCH3 | H | H | H | CH3 | OCH3 | CH3 |
| SO | H | H | —O—CH—O— (methylenedioxy R2/R3) | | H | H | CH3 | OCH3 | CH3 |
| SO | H | H | —O—CH—O— (methylenedioxy R2/R3) | | H | H | CH3 | OCH3 | CH3 |
| S | H | H | CH(OCH3)2 | H | H | H | CH3 | OCH3 | CH3 |
| SO | H | H | CH(OCH3)2 | H | H | H | CH3 | OCH3 | CH3 |
| S | H | H | CHO | H | H | H | CH3 | OCH3 | CH3 |
| SO | H | H | CHO | H | H | H | CH3 | OCH3 | CH3 |

TABLE 1-continued

Illustrative examples of compounds included in the scope of the invention.

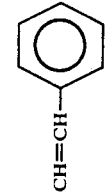

| X | R15 | R1 | R2 | R3 | R4 | R5 | R6 | R7 | R8 |
|---|---|---|---|---|---|---|---|---|---|
| S | H | H | CH=CH—COOC2H5 | H | H | H | CH3 | OCH3 | CH3 |
| SO | H | H | CH=CH—COOC2H5 | H | H | H | CH3 | OCH3 | CH3 |
| S | H | H | CH2CH2COOC2H5 | H | H | H | CH3 | OCH3 | CH3 |
| SO | H | H | CH2CH2COOC2H5 | H | H | H | CH3 | OCH3 | CH3 |
| S | H | H | CH2CH2CON(CH3)2 | H | H | H | CH3 | OCH3 | CH3 |
| SO | H | H | CH2CH2CON(CH3)2 | H | H | H | CH3 | OCH3 | CH3 |
| S | H | H | CH=CH—CN | H | H | H | CH3 | OCH3 | CH3 |
| SO | H | H | CH=CH—CN | H | H | H | CH3 | OCH3 | CH3 |
| S | H | H | CH2CH2CN | H | H | H | CH3 | OCH3 | CH3 |
| SO | H | H | CH2CH2CN | H | H | H | CH3 | OCH3 | CH3 |
| S | H | H | CH2CH2CH2OH | H | H | H | CH3 | OCH3 | CH3 |
| SO | H | H | CH2CH2CH2OH | H | H | H | CH3 | OCH3 | CH3 |
| S | H | H | CH2CH2CH2OCOCH3 | H | H | H | CH3 | OCH3 | CH3 |
| SO | H | H | CH2CH2CH2OCOCH3 | H | H | H | CH3 | OCH3 | CH3 |
| S | H | H | CH2CH2CH2N(CH3)2 | H | H | H | CH3 | OCH3 | CH3 |
| SO | H | H | CH2CH2CH2N(CH3)2 | H | H | H | CH3 | OCH3 | CH3 |
| S | H | H | CH2CH2CH2NHCOC2H5 | H | H | H | CH3 | OCH3 | CH3 |
| SO | H | H | CH2CH2CH2NHCOC2H5 | H | H | H | CH3 | OCH3 | CH3 |
| S | H | H | CH=CHCOCH3 | H | H | H | CH3 | OCH3 | CH3 |
| SO | H | H | CH=CHCOCH3 | H | H | H | CH3 | OCH3 | CH3 |
| S | H | H | CH2CH2COCH3 | H | H | H | CH3 | OCH3 | CH3 |
| SO | H | H | CH2CH2COCH3 | H | H | H | CH3 | OCH3 | CH3 |
| S | H | H | CH=CH—C6H5 | H | H | H | CH3 | OCH3 | CH3 |
| SO | H | H | CH=CH—C6H5 | H | H | H | CH3 | OCH3 | CH3 |

TABLE 1-continued
Illustrative examples of compounds included in the scope of the invention.

| X | R15 | R1 | R2 | R3 | R4 | R5 | R6 | R7 | R8 |
|---|-----|----|----|----|----|----|----|----|----|
| S | H | H | -CH₂CH₂-C₆H₅ | H | H | H | CH₃ | OCH₃ | CH₃ |
| SO | H | H | -CH₂CH₂-C₆H₅ | H | H | H | CH₃ | OCH₃ | CH₃ |
| S | H | CH₃ | H | CH₃ | H | H | CH₃ | OCH₂CH=CH₂ | CH₃ |
| SO | H | CH₃ | H | CH₃ | H | H | CH₃ | OCH₂CH=CH₂ | CH₃ |
| S | H | H | -CH₂-C₆H₅ | H | H | H | CH₃ | OCH₃ | CH₃ |
| SO | H | H | -CH₂-C₆H₅ | H | H | H | CH₃ | OCH₃ | CH₃ |
| S | H | H | -O-C₆H₅ | H | H | H | CH₃ | OCH₃ | CH₃ |
| SO | H | H | -O-C₆H₅ | H | H | H | CH₃ | OCH₃ | CH₃ |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| S | H | H | OCH2-C6H5 | H | H | H | CH3 | OCH3 | CH3 |
| SO | H | H | OCH2-C6H5 | H | H | H | CH3 | OCH3 | CH3 |
| S | H | H | OCH2CN | H | H | H | CH3 | OCH3 | CH3 |
| SO | H | H | OCH2CN | H | H | H | CH3 | OCH3 | CH3 |
| S | H | H | OCH2COOC2H5 | H | H | H | CH3 | OCH3 | CH3 |
| SO | H | H | OCH2COOC2H5 | H | H | H | CH3 | OCH3 | CH3 |
| S | H | H | OCH2CH2OH | H | H | H | CH3 | OCH3 | CH3 |
| SO | H | H | OCH2CH2OH | H | H | H | CH3 | OCH3 | CH3 |
| S | H | H | OCH2CH2OCOCH2-C6H5 | H | H | H | CH3 | OCH3 | CH3 |
| SO | H | H | OCH2CH2OCOCH2-C6H5 | H | H | H | CH3 | OCH3 | CH3 |
| S | H | H | OCH2CH2NH2 | H | H | H | CH3 | OCH3 | CH3 |
| SO | H | H | OCH2CH2NH2 | H | H | H | CH3 | OCH3 | CH3 |
| S | H | H | OCH2CH2NHCOCH(CH3)2 | H | H | H | CH3 | OCH3 | CH3 |
| SO | H | H | OCH2CH2NHCOCH(CH3)2 | H | H | H | CH3 | OCH3 | CH3 |

TABLE 1-continued

Illustrative examples of compounds included in the scope of the invention.

| X | R¹⁵ | R¹ | R² | R³ | R⁴ | R⁵ | R⁶ | R⁷ | R⁸ |
|---|---|---|---|---|---|---|---|---|---|
| S | H | H | OCH₂CO-C₆H₅ | H | H | H | CH₃ | OCH₃ | CH₃ |
| SO | H | H | OCH₂CO-C₆H₅ | H | H | H | CH₃ | OCH₃ | CH₃ |
| S | H | H | CO-C₆H₅ | H | H | H | CH₃ | OCH₃ | CH₃ |
| SO | H | H | CO-C₆H₅ | H | H | H | CH₃ | OCH₃ | CH₃ |
| S | H | H | CO(CH₂)₃O-C₆H₅ | H | H | H | CH₃ | OCH₃ | CH₃ |
| SO | H | H | CO(CH₂)₃O-C₆H₅ | H | H | H | CH₃ | OCH₃ | CH₃ |

TABLE 1-continued

Illustrative examples of compounds included in the scope of the invention.

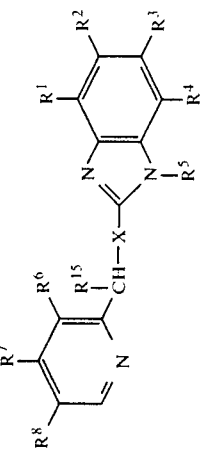

| X | R¹⁵ | R¹ | R² | R³ | R⁴ | R⁵ | R⁶ | R⁷ | R⁸ |
|---|---|---|---|---|---|---|---|---|---|
| S | H | H | ![cyclohexyl] | H | H | H | CH₃ | OCH₃ | CH₃ |
| SO | H | H | ![cyclohexyl] | H | H | H | CH₃ | OCH₃ | CH₃ |
| S | H | H | COOCH₂CH₂OCH₃ | CH₃ | H | H | CH₃ | OCH₃ | CH₃ |
| SO | H | H | COOCH₂CH₂OCH₃ | CH₃ | H | H | CH₃ | OCH₃ | CH₃ |
| S | H | H | ![phenyl]-COOCH₂- | CH₃ | H | H | CH₃ | OCH₃ | CH₃ |
| SO | H | H | ![phenyl]-COOCH₂- | CH₃ | H | H | CH₃ | OCH₃ | CH₃ |
| S | H | H | CH₂OH | CH₃ | H | H | CH₃ | OCH₃ | CH₃ |
| SO | H | H | CH₂OH | CH₃ | H | H | CH₃ | OCH₃ | CH₃ |
| S | H | H | ![phenyl]-CH₂OCO- | CH₃ | H | H | CH₃ | OCH₃ | CH₃ |

TABLE 1-continued

Illustrative examples of compounds included in the scope of the invention.

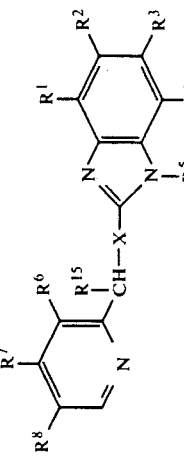

| X | R$^{15}$ | R$^1$ | R$^2$ | R$^3$ | R$^4$ | R$^5$ | R$^6$ | R$^7$ | R$^8$ |
|---|---|---|---|---|---|---|---|---|---|
| SO | H | H | CH$_2$OCO-C$_6$H$_5$ | CH$_3$ | H | H | CH$_3$ | OCH$_3$ | CH$_3$ |
| S | H | H | COOCH$_3$ | CH$_3$ | H | H | CH$_3$ | OCH$_2$CH=CH$_2$ | CH$_3$ |
| SO | H | H | COOCH$_3$ | CH$_3$ | H | H | CH$_3$ | OCH$_2$CH=CH$_2$ | CH$_3$ |
| S | H | H | CH$_2$CH$_2$OCH$_3$ | H | H | H | CH$_3$ | OCH$_3$ | CH$_3$ |
| SO | H | H | CH$_2$CH$_2$OCH$_3$ | H | H | H | CH$_3$ | OCH$_3$ | CH$_3$ |
| S | H | H | CH(CH$_3$)$_2$ | H | H | H | CH$_3$ | OCH$_2$CH=CH$_2$ | CH$_3$ |
| SO | H | H | CH(CH$_3$)$_2$ | H | H | H | CH$_3$ | OCH$_2$CH=CH$_2$ | CH$_3$ |
| S | H | H | C(CH$_3$)$_3$ | H | H | H | CH$_3$ | OCH$_3$ | CH$_3$ |
| SO | H | H | C(CH$_3$)$_3$ | H | H | H | CH$_3$ | OCH$_3$ | CH$_3$ |
| S | H | CH$_3$ | OCH$_3$ | CH$_3$ | H | H | CH$_3$ | OCH$_3$ | CH$_3$ |
| SO | H | CH$_3$ | OCH$_3$ | CH$_3$ | H | H | CH$_3$ | OCH$_3$ | CH$_3$ |
| S | H | CH$_3$ | OCH$_3$ | CH$_3$ | H | H | CH$_3$ | CH$_3$ | CH$_3$ |
| SO | H | CH$_3$ | OCH$_3$ | CH$_3$ | H | H | CH$_3$ | CH$_3$ | CH$_3$ |
| S | H | CH$_3$ | OCH$_2$CH$_2$OCH$_3$ | CH$_3$ | H | H | CH$_3$ | OCH$_3$ | H |
| SO | H | CH$_3$ | OCH$_2$CH$_2$OCH$_3$ | CH$_3$ | H | H | CH$_3$ | OCH$_3$ | H |
| S | H | CH$_3$ | OCH$_2$CH$_2$OCH$_3$ | CH$_3$ | H | H | H | CH$_3$ | CH$_3$ |
| SO | H | CH$_3$ | OCH$_2$CH$_2$OCH$_3$ | CH$_3$ | H | H | H | CH$_3$ | CH$_3$ |
| S | H | CH$_3$ | COCH$_3$ | CH$_3$ | H | H | CH$_3$ | OCH$_3$ | CH$_3$ |
| SO | H | CH$_3$ | COCH$_3$ | CH$_3$ | H | H | CH$_3$ | OCH$_3$ | CH$_3$ |
| S | H | CH$_3$ | COCH$_3$ | CH$_3$ | H | H | CH$_3$ | CH$_3$ | CH$_3$ |
| SO | H | CH$_3$ | COCH$_3$ | CH$_3$ | H | H | CH$_3$ | CH$_3$ | CH$_3$ |
| S | H | CH$_3$ | COC$_2$H$_5$ | CH$_3$ | H | H | CH$_3$ | OCH$_3$ | CH$_3$ |
| SO | H | CH$_3$ | COC$_2$H$_5$ | CH$_3$ | H | H | CH$_3$ | OCH$_3$ | CH$_3$ |
| S | CH$_3$ | CH$_3$ | CH$_3$ | CH$_3$ | H | H | CH$_3$ | CH$_3$ | CH$_3$ |
| SO | CH$_3$ | CH$_3$ | CH$_3$ | CH$_3$ | H | H | CH$_3$ | CH$_3$ | CH$_3$ |
| S | H | CH$_3$ | CH$_3$ | CH$_3$ | H | H | CH$_3$ | OCH$_3$ | H |
| SO | H | CH$_3$ | CH$_3$ | CH$_3$ | H | H | CH$_3$ | OCH$_3$ | H |
| S | H | CH$_3$ | C$_2$H$_5$ | CH$_3$ | H | H | CH$_3$ | OCH$_3$ | CH$_3$ |
| SO | H | CH$_3$ | C$_2$H$_5$ | CH$_3$ | H | H | CH$_3$ | OCH$_3$ | CH$_3$ |
| S | H | CH$_3$ | C$_2$H$_5$ | CH$_3$ | H | H | CH$_3$ | OCH$_3$ | CH$_3$ |
| SO | H | CH$_3$ | CH(CH$_3$)$_2$ | CH$_3$ | H | H | CH$_3$ | OCH$_3$ | CH$_3$ |
| S | H | CH$_3$ | CH(CH$_3$)$_2$ | CH$_3$ | H | H | CH$_3$ | OCH$_3$ | CH$_3$ |
| SO | H | CH$_3$ | CH(CH$_3$)$_2$ | CH$_3$ | H | H | CH$_3$ | OCH$_3$ | CH$_3$ |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| S | H | CH3 | CH(CH3)2 | CH3 | H | H | CH3 | CH3 | CH3 |
| SO | H | CH3 | CH(CH3)2 | CH3 | H | H | CH3 | CH3 | CH3 |
| S | H | CH3 | COCH2–C6H5 | CH3 | H | H | CH3 | OCH3 | CH3 |
| SO | H | CH3 | COCH2–C6H5 | CH3 | H | H | CH3 | OCH3 | CH3 |
| S | H | OCH3 | Br | OCH3 | H | H | CH3 | OCH3 | CH3 |
| SO | H | OCH3 | Br | OCH3 | H | H | CH3 | OCH3 | CH3 |
| S | H | OCH3 | Br | OCH3 | H | H | CH3 | CH3 | H |
| SO | H | OCH3 | Br | OCH3 | H | H | CH3 | CH3 | H |
| S | H | C2H5 | CN | C2H5 | H | H | CH3 | OCH3 | CH3 |
| SO | H | C2H5 | CN | C2H5 | H | H | CH3 | OCH3 | CH3 |
| S | H | C2H5 | CN | C2H5 | H | H | CH3 | OC2H5 | CH3 |
| SO | H | CH3 | CN | CH3 | H | H | CH3 | OC2H5 | CH3 |
| S | H | CH3 | OCH3 | CH3 | CH3 | H | CH3 | OCH3 | CH3 |
| SO | H | CH3 | OCH3 | CH3 | CH3 | H | CH3 | OCH3 | CH3 |
| S | H | CH3 | OCH3 | H | CH3 | H | CH3 | OCH3 | CH3 |
| SO | H | CH3 | OCH3 | H | OCH3 | H | CH3 | OCH3 | CH3 |
| S | H | Cl | OCH3 | H | OCH3 | H | CH3 | OCH3 | CH3 |
| SO | H | Cl | Cl | Cl | H | H | CH3 | OCH3 | CH3 |
| S | H | Cl | Cl | Cl | H | H | CH3 | OCH3 | CH3 |
| SO | H | Cl | Cl | Cl | Cl | H | CH3 | OCH2CH=CH2 | CH3 |
| S | H | Cl | Cl | Cl | Cl | H | CH3 | OCH2CH=CH2 | CH3 |
| SO· | H | Cl | Cl | Cl | Cl | H | CH3 | OCH3 | CH3 |
| S | H | Cl | Cl | H | Cl | H | CH3 | OCH2CH=CH2 | CH3 |
| SO | H | Cl | Cl | H | Cl | H | CH3 | OCH2CH=CH2 | CH3 |
| S | H | OCH3 | Br | H | OCH3 | H | CH3 | OCH3 | CH3 |
| SO | H | OCH3 | Br | H | OCH3 | H | CH3 | OCH3 | CH3 |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| S | H | OCH3 | Cl | Cl | OC2H5 | H | CH3 | OCH3 | CH3 |
| SO | H | OCH3 | Cl | Cl | OC2H5 | H | CH3 | OCH3 | CH3 |
| S | H | OCH3 | Cl | Cl | OC2H5 | H | CH3 | OCH3 | H |
| SO | H | OCH3 | Cl | Cl | CH3 | H | CH3 | CH3 | H |
| S | H | COCH3 | CH3 | CH3 | CH3 | H | CH3 | OCH3 | CH3 |
| SO | H | COCH3 | CH3 | CH3 | CH3 | H | CH3 | OCH3 | CH3 |
| S | H | F | Cl | H | Cl | H | CH3 | OCH3 | CH3 |
| SO | H | F | Cl | H | H | H | CH3 | OCH3 | CH3 |
| S | H | Cl | CH2COOCH3 | Cl | Cl | H | CH3 | OCH3 | CH3 |
| SO | H | Cl | CH2COOCH3 | Cl | Cl | H | CH3 | OCH3 | CH3 |
| S | H | Cl | CH2CN | Cl | Cl | H | CH3 | OCH3 | CH3 |
| SO | H | Cl | —CH=CH—CH=CH— | | Cl | H | CH3 | OCH3 | CH3 |
| S | H | H | (2-methylpiperidin-1-yl)CON | —CH=CH—CH=CH— | | H | CH3 | OCH3 | CH3 |
| SO | H | H | (2-methylpiperidin-1-yl)CON | H | H | H | CH3 | OCH3 | CH3 |
| S | H | H | phenyl | H | H | H | CH3 | OCH3 | CH3 |
| SO | H | H | phenyl | H | H | H | CH3 | OCH3 | CH3 |

TABLE 1-continued

Illustrative examples of compounds included in the scope of the invention.

| X | R15 | R1 | R2 | R3 | R4 | R5 | R6 | R7 | R8 |
|---|-----|----|----|----|----|----|----|----|----|
| S | H | H | —OCH$_2$O— | | H | H | CH$_3$ | OCH$_3$ | CH$_3$ |
| SO | H | H | —OCH$_2$O— | | H | H | CH$_3$ | OCH$_3$ | CH$_3$ |
| S | H | H | —OCH$_2$O— | | H | H | CH$_3$ | CH$_3$ | CH$_3$ |
| SO | H | H | —OCH$_2$O— | | H | H | CH$_3$ | CH$_3$ | CH$_3$ |
| S | H | H | spiro-cyclohexane-1,1-dioxy | | H | H | CH$_3$ | OCH$_3$ | CH$_3$ |
| SO | H | H | spiro-cyclohexane-1,1-dioxy | | H | H | CH$_3$ | OCH$_3$ | CH$_3$ |
| S | H | H | —CH=CH—CH=N— | | H | H | CH$_3$ | OCH$_3$ | CH$_3$ |
| SO | H | H | —CH=CH—CH=N— | | H | H | CH$_3$ | OCH$_3$ | CH$_3$ |
| S | H | H | —CH=CH—CH=CH— | | H | H | CH$_3$ | OCH$_3$ | CH$_3$ |
| SO | H | H | —CH=CH—CH=CH— | | H | H | CH$_3$ | OCH$_3$ | CH$_3$ |
| S | H | OCH$_3$ | —CH=CH—CH=CH— | | H | H | CH$_3$ | OCH$_3$ | CH$_3$ |
| SO | H | OCH$_3$ | —CH=CH—CH=CH— | | H | H | CH$_3$ | OCH$_3$ | CH$_3$ |
| S | H | OCH$_3$ | —CH$_2$CH$_2$CH$_2$— | | Cl | H | CH$_3$ | OCH$_3$ | CH$_3$ |
| SO | H | OCH$_3$ | —CH$_2$CH$_2$CH$_2$— | | Cl | H | CH$_3$ | OCH$_3$ | CH$_3$ |
| S | H | H | —CH$_2$CH$_2$CH$_2$— | | Cl | H | CH$_3$ | OC$_2$H$_5$ | CH$_3$ |
| SO | H | H | —CH$_2$CH$_2$CH$_2$— | | Cl | H | CH$_3$ | OC$_2$H$_5$ | CH$_3$ |
| S | H | H | —CH=CH—CH=C(—CH$_2$CH$_2$—)— | | H | H | CH$_3$ | OCH$_3$ | CH$_3$ |
| SO | H | H | —CH=CH—CH=C(—CH$_2$CH$_2$—)— | | H | H | CH$_3$ | OCH$_3$ | CH$_3$ |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| S | H | H | | 2-methylbenzoyl | H | H | CH3 | OCH3 | CH3 |
| SO | H | H | | 2-methylbenzoyl | H | H | CH3 | OCH3 | CH3 |
| S | H | H | | —OCH2O— | H | CO2CH3 | CH3 | OCH3 | CH3 |
| SO | H | H | | —OCH2O— | H | CO2CH3 | CH3 | OCH3 | CH3 |
| S | H | H | | —OCH2O— | H | CO2C2H5 | CH3 | OCH3 | CH3 |
| SO | H | H | | —OCH2O— | H | CO2C2H5 | CH3 | OCH3 | CH3 |
| S | H | H | | —OCH2O— | H | CO2C(CH3)3 | CH3 | OCH3 | CH3 |
| SO | H | H | | —OCH2O— | H | CO2C(CH3)3 | CH3 | OCH3 | CH3 |
| S | H | H | | —OCH2O— | H | CO2CH2—C6H5 | CH3 | OCH3 | CH3 |
| SO | H | H | | —OCH2O— | H | CO2CH2—C6H5 | CH3 | OCH3 | CH3 |

TABLE 1-continued

Illustrative examples of compounds included in the scope of the invention.

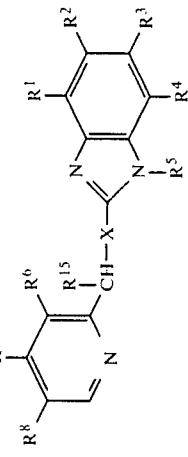

| X | R$^{15}$ | R$^1$ | R$^2$ | R$^3$ | R$^4$ | R$^5$ | R$^6$ | R$^7$ | R$^8$ |
|---|---|---|---|---|---|---|---|---|---|
| S | H | H | | —OCH$_2$O— | H | C$_6$H$_5$CO | CH$_3$ | OCH$_3$ | CH$_3$ |
| SO | H | H | | —OCH$_2$O— | H | C$_6$H$_5$CO | CH$_3$ | OCH$_3$ | CH$_3$ |
| S | H | H | | —OCH$_2$O— | H | CONH$_2$ | CH$_3$ | OCH$_3$ | CH$_3$ |
| SO | H | H | | —OCH$_2$O— | H | CONH$_2$ | CH$_3$ | OCH$_3$ | CH$_3$ |
| S | H | H | | —OCH$_2$O— | H | CONHC$_2$H$_5$ | CH$_3$ | OCH$_3$ | CH$_3$ |
| SO | H | H | | —OCH$_2$O— | H | CONHC$_2$H$_5$ | CH$_3$ | OCH$_3$ | CH$_3$ |
| S | H | H | | —OCH$_2$O— | H | CONHCH$_2$C$_6$H$_5$ | CH$_3$ | OCH$_3$ | CH$_3$ |
| SO | H | H | | —OCH$_2$O— | H | CONHCH$_2$C$_6$H$_5$ | CH$_3$ | OCH$_3$ | CH$_3$ |
| S | H | H | | —OCH$_2$O— | H | CONHC$_6$H$_5$ | CH$_3$ | OCH$_3$ | CH$_3$ |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| SO | H | H |  | —OCH$_2$O— | H | CONH-Ph | CH$_3$ | OCH$_3$ | CH$_3$ |
| S | H | H | CH$_3$ | —OCH$_2$O— | H | CON(CH$_3$)$_2$ | CH$_3$ | OCH$_3$ | CH$_3$ |
| SO | H | H | CH$_3$ | —OCH$_2$O— | H | CON(CH$_3$)$_2$ | CH$_3$ | OCH$_3$ | CH$_3$ |
| S | H | CH$_3$ | OCH$_3$ | CH$_3$ | H | H | CH$_3$ | OCH$_2$CH$_2$OCH$_3$ | CH$_3$ |
| SO | H | CH$_3$ | OCH$_3$ | CH$_3$ | H | H | CH$_3$ | OCH$_2$CH$_2$OCH$_3$ | CH$_3$ |
| S | H | H | OCH$_3$ | H | H | H | H | —CH=CH—O— | H |
| SO | H | H | OCH$_3$ | H | H | H | H | —CH=CH—O— | H |
| S | H | H | OCH$_3$ | H | H | H | H | —O—CH=CH— | H |
| SO | H | H | OCH$_3$ | H | H | H | H | —O—CH=CH— | H |
| S | H | H | OCH$_3$ | H | H | H | H | —CH=CH—NH— | H |
| SO | H | H | OCH$_3$ | H | H | H | H | —CH=CH—NH— | H |
| S | H | H | OCH$_3$ | H | H | H | H | —NH—CH=CH— | H |
| SO | H | H | OCH$_3$ | H | H | H | H | —NH—CH=CH— | H |
| S | H | H | OCH$_3$ | H | H | H | H | —CH=CH—N(CH$_3$)— | H |
| SO | H | H | OCH$_3$ | H | H | H | H | —CH=CH—N(CH$_3$)— | H |
| S | H | CH$_3$ | OCH$_3$ | CH$_3$ | H | H | CH$_3$ | —N(CH$_3$)—CH=CH— | CH$_3$ |
| SO | H | CH$_3$ | OCH$_3$ | CH$_3$ | H | H | CH$_3$ | —N(CH$_3$)—CH=CH— | CH$_3$ |
| S | H | H | CH$_2$C≡CH | H | H | H | CH$_3$ | OCH$_3$ | CH$_3$ |
| SO | H | H | CH$_2$C≡CH | H | H | H | CH$_3$ | OCH$_3$ | CH$_3$ |
| S | H | H | CH$_2$CH$_2$CH$_2$O-Ph | H | H | H | CH$_3$ | OCH$_3$ | CH$_3$ |
| SO | H | H | CH$_2$CH$_2$CH$_2$O-Ph | H | H | H | CH$_3$ | OCH$_3$ | CH$_3$ |

TABLE 1-continued

Illustrative examples of compounds included in the scope of the invention.

| X | R¹⁵ | R¹ | R² | R³ | R⁴ | R⁵ | R⁶ | R⁷ | R⁸ |
|---|---|---|---|---|---|---|---|---|---|
| S | H | H | $OCH_2CH_2CH_2O$–C₆H₅ | H | H |  | $CH_3$ | $OCH_3$ | $CH_3$ |
| SO | H | H | $OCH_2CH_2CH_2O$–C₆H₅ | H | H |  | $CH_3$ | $OCH_3$ | $CH_3$ |
| S | H | $CH_3$ | $O(CH_2)_6CH_3$ | $CH_3$ | H |  | $CH_3$ | $OCH_3$ | $CH_3$ |
| SO | H | $CH_3$ | $O(CH_2)_6CH_3$ | $CH_3$ | H |  | $CH_3$ | $OCH_3$ | $CH_3$ |
| S | H | H | $C_2H_5$ | H | H |  | $CH_3$ | $OCH_2CH=CH_2$ | $CH_3$ |
| SO | H | H | $C_2H_5$ | H | H |  | $CH_3$ | $OCH_2CH=CH_2$ | $CH_3$ |
| S | H | H | $OCH_3$ | H | H | CO–C₆H₅ | $CH_3$ | $OCH_3$ | $CH_3$ |
| S | H | H | H | $OCH_3$ | H | CO–C₆H₅ | $CH_3$ | $OCH_3$ | $CH_3$ |
| SO | H | H | $OCH_3$ | H | H | CO–C₆H₅ | $CH_3$ | $OCH_3$ | $CH_3$ |

TABLE 1-continued

Illustrative examples of compounds included in the scope of the invention.

| X | R$^{15}$ | R$^1$ | R$^2$ | R$^3$ | R$^4$ | R$^5$ | R$^6$ | R$^7$ | R$^8$ |
|---|---|---|---|---|---|---|---|---|---|
| SO | H | H | H | OCH$_3$ | H | ⌬—CO— | CH$_3$ | OCH$_3$ | CH$_3$ |
| S | H | H | CH$_3$ | CH$_2$OCO—⌬ | H | ⌬—CO— | CH$_3$ | OCH$_3$ | CH$_3$ |
| S | H | H | CH$_3$ | CH$_3$ | H | ⌬—CO— | CH$_3$ | OCH$_3$ | CH$_3$ |
| S | H | H | —OCH$_2$O— | —OCH$_2$O— | H | COC$_2$H$_5$ | CH$_3$ | OCH$_3$ | CH$_3$ |
| SO | H | H | —OCH$_2$O— | —OCH$_2$O— | H | COC$_2$H$_5$ | CH$_3$ | OCH$_3$ | CH$_3$ |
| SO | H | H | CH$_3$ | CH$_3$ | H | COOCH$_3$ | CH$_3$ | OCH$_3$ | CH$_3$ |
| S | H | H | ⌬(2-CO—, 1-OC—) | H | H | CH$_3$ | OCH$_3$ | CH$_3$ |
| SO | H | H | ⌬(2-CO—, 1-OC—) | H | H | CH$_3$ | OCH$_3$ | CH$_3$ |
| S | H | H | SCH$_3$ | H | H | H | CH$_3$ | OCH$_3$ | CH$_3$ |

TABLE 1-continued

Illustrative examples of compounds included in the scope of the invention.

| X | R15 | R1 | R2 | R3 | R4 | R5 | R6 | R7 | R8 |
|---|---|---|---|---|---|---|---|---|---|
| S | H | H | CH(CH3)2 | H | H | H | CH3 | OCH2-(tetrahydropyran) | CH3 |
| SO | H | H | CH(CH3)2 | H | H | H | CH3 | OCH2-(tetrahydropyran) | CH3 |
| S | H | H | CH2CH2COCH3 | H | H | H | CH3 | OCH2CH=CH2 | CH3 |
| SO | H | H | CH2CH2COCH3 | H | H | H | CH3 | OCH2CH=CH2 | CH3 |
| SO | H | H | CH3 | CH3 | H | H | CH3 | OCH3 | CH3 |
| SO | H | H | CH3 | CH3 | H | COOC(CH3)3 | CH3 | OCH3 | CH3 |
| SO | H | H | CH3 | CH3 | H | CON(CH3)2 | CH3 | OCH3 | CH3 |
| SO | H | H | CH3 | H | H | CON(CH3)2 | CH3 | OCH3 | CH3 |
| S | H | H | Br | H | H | H | CH3 | OCH3 | CH3 |
| SO | H | H | Br | H | H | H | CH3 | OCH3 | CH3 |
| S | H | CH3 | CH3 | CH3 | H | H | CH3 | OCH2CH=CH2 | CH3 |
| SO | H | CH3 | CH3 | CH3 | H | H | CH3 | OCH2CH=CH2 | CH3 |
| S | H | CH3 | CH3 | CH3 | H | H | CH3 | CH3 | H |
| SO | H | CH3 | CH3 | CH3 | H | H | H | CH3 | H |
| SO | H | CH3 | CH3 | CH3 | H | H | CH3 | CH3 | CH3 |
| S | H | CH3 | CH3 | CH3 | CH3 | H | CH3 | CH3 | CH3 |
| SO | H | CH3 | CH3 | CH3 | CH3 | H | CH3 | CH3 | CH3 |
| SO | H | CH3 | CH3 | —CH2CH2CH2— | H | H | H | H | CH3 |
| S | H | CH3 | CH3 | —CH2CH2CH2— | H | H | CH3 | OC2H5 | CH3 |
| SO | H | CH3 | CH3 | —CH2CH2CH2— | H | H | CH3 | OC2H5 | CH3 |
| S | H | H | CN | H | H | H | CH3 | OCH3 | C2H5 |
| SO | H | H | CN | H | H | H | CH3 | OCH3 | C2H5 |
| SO | H | H | COOCH3 | H | H | H | CH3 | OCH3 | CH3 |
| SO | H | H | OCH3 | H | H | H | H | —CH2CH2CH2O— | H |
| S | H | H | OCH3 | H | H | H | CH3 | —OCH2CH2— | CH3 |
| S | H | H | SOCH3 | H | H | H | CH3 | OCH3 | CH3 |
| SO | H | H | SOCH3 | H | H | H | CH3 | OCH3 | CH3 |

TABLE 1-continued

Illustrative examples of compounds included in the scope of the invention.

| X | R$^{15}$ | R$^1$ | R$^2$ | R$^3$ | R$^4$ | R$^5$ | R$^6$ | R$^7$ | R$^8$ |
|---|---|---|---|---|---|---|---|---|---|
| S | H | H | CH$_3$ | CH$_3$ | H | H | CH$_3$ | —OCH$_2$-(tetrahydrofuran-2-yl) | CH$_3$ |
| SO | H | H | CH$_3$ | CH$_3$ | H | H | CH$_3$ | —OCH$_2$-(tetrahydrofuran-2-yl) | CH$_3$ |
| S | H | H | —CH=CH—CH=CH— | H | —CH=CH—CH=CH— | H | CH$_3$ | OCH$_3$ | CH$_3$ |
| SO | H | H | NO$_2$ | H | H | H | CH$_3$ | OCH$_3$ | CH$_3$ |
| S | H | H | CF$_3$ | H | H | H | CH$_3$ | OCH$_2$-(tetrahydrofuran-2-yl) | CH$_3$ |
| SO | H | H | CF$_3$ | H | H | H | CH$_3$ | OCH$_2$-(tetrahydrofuran-2-yl) | CH$_3$ |
| S | H | H | CH$_2$CH$_2$COOC$_2$H$_5$ | H | H | O=C—OC(CH$_3$)$_3$ | CH$_3$ | OCH$_3$ | CH$_3$ |
| SO | H | H | OCH$_3$ | H | H | H | CH$_3$ | OCH$_3$ | CH$_3$ |
| SO | H | H | CH$_3$ | CH$_3$ | H | H | H | OCH$_3$ | C$_2$H$_5$ |

The invention takes into consideration that compounds that structurally deviate from the formula I, after administration to a living organism may be transformed to a compound of formula I and in this structural form exert their effect. Such compunds structurally deviating from compounds of the formula I, are included in the scope of the invention.

Likewise, certain compounds of formula I may be metabolized into other compounds of formula I before exerting their effect. Compounds of the invention wherein X is S are thus believed to exert their antisecretory and cytoprotective activities after metabolism to compounds wherein X is SO and compounds of the invention wherein $R^5$ is $R^{14}CO$ are believed to exert antisecretory and cytoprotective activity after metabolism to compounds wherein $R^5$ is H. These considerations are also a further aspect of the invention.

Further, it is believed that all compounds of formula I wherein X is SO after administration to a living organism, exert their antisecretory and cytoprotective effects after metabolic or pure chemical transformation to another, reactive species. Accordingly, the same is true also for the compounds of formula I wherein X is S, but via initial transformation to the corresponding compounds of formula I wherein X is SO. These consierations as well as such reactive species per se are included within the scope of the present invention.

Some of the compounds of the formula I exhibit increased aqueous solubility. This property is particularly pronounced for compounds of the formula I wherein at least one of the substituents $R^1$, $R^2$, $R^3$ and $R^4$ is —(Z-)$_n$—A—D wherein n, Z, A and D are combined as follows: n is O; A is as defined previously; and D is

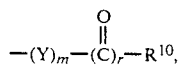

wherein m is 1, Y is —O—, r is O and $R^{10}$ is H. This combination accordingly means that the group —(Z-)$_n$—A—D is —A—OH.

PREPARATION

Compounds of formula I above may be prepared according to the following methods:

a) Oxidizing a compound of the formula I,

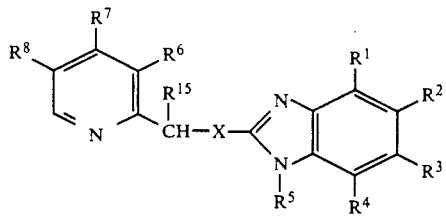

wherein X is S and $R^{15}$, $R^1$, $R^2$, $R^3$, $R^4$, $R^5$, $R^6$, $R^7$ and $R^8$ have the meanings given, to give a compound of the same formula I wherein X is SO. This oxidation may be carried out by using an oxidizing agent selected from the group consisting of nitric acid, hydrogen peroxide, peracids, peresters, ozone, dinitrogentetraoxide, iodosobenzene, N-halosuccinimide, 1-chlorobenzotriazole, t-butylhypochlorite, diazabicyclo-[2,2,2]-octane bromine complex, sodium metaperiodate, selenium dioxide, manganese dioxide, chromic acid, cericammonium nitrate, bromine, chlorine, and sulfuryl chloride. The oxidation usually takes place in a solvent wherein the oxidizing agent is present in some excess in relation to the product to be oxidized.

The oxidation may also be carried out enzymatically by using an oxidating enzyme or microbiotically by using a suitable microorganism.

b) Reacting a compound of the formula

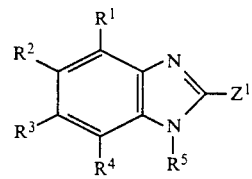

with a compound of the formula

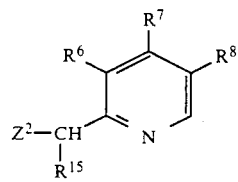

in which formulas $R^{15}$, $R^1$, $R^2$, $R^3$, $R^4$, $R^5$, $R^6$, $R^7$ and $R^8$ are as defined previously and wherein one of $Z^1$ and $Z^2$ is SH and the other is a leaving group, gives a compound of the formula I wherein X is S.

Examples of leaving groups $Z^1$ and $Z^2$ in the compounds II and III are halogens, preferably chlorine, bromine or iodine, acyloxy radicals, for example residues of strong organic sulfonic acids, for instance of an arylsulfonic acid, for example tosyloxy or an alkylsulfonic acid, for example mesyloxy, alkylmercapto groups, for example methylmercapto, alkylsulfinyl groups, for example methylsulfinyl and the like.

Thus, $Z^1$ or $Z^2$ when designating leaving groups may be a reactive esterified hydroxy group. The esterification may be carried out with an organic acid or with an inorganic acid such as HCl, HBr or $H_2SO_4$.

The reaction of a compound of formula II above with a compound of formula III is conveniently carried out in the presence of a suitable solvent that is inert under the reaction conditions utilized as described hereinafter. The reaction may further be carried out in the presence of a suitable base. Suitable bases include, for example, inorganic bases such as sodium or potassium hydroxide, sodium or potassium alkoxide, sodium or potassium hydride and the like, organic bases such as tertiary amines, for example triethylamine and the like. Suitable solvents for the above described reaction include, for example, alcohols, preferably lower alkanols such as methanol and ethanol, mixtures of such alcohols with water, ethers, such as tetrahydrofuran, halogenated hydrocarbons, such as methylene chloride. Aprotic solvents such as ethers and halogenated carbons are necessary in the case of sodium and potassium hydride.

The reaction of the compounds of formulas II and III may be carried out at a temperature between the ambient temperature and the boiling temperature of the reaction mixture. It is preferred to carry out the reaction, however, at a temperature at or close to the boiling point of the reaction mixture for the preparation of a compound of the formula I wherein $R^5$ is H.

c) Esterification of a compound of the formula

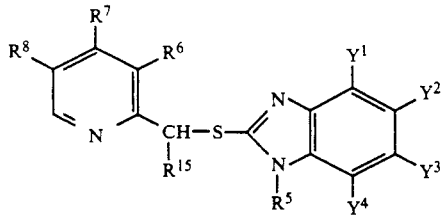

IV wherein $R^{15}$, $R^5$, $R^6$, $R^7$ and $R^8$ are as defined above and $Y^1$, $Y^2$, $Y^3$ and $Y^4$ represent either $R^1$, $R^2$, $R^3$ and $R^4$ according to the above definition, respectively, or the groups $(Z)_n$—A—COOH, COOH and $(Z)_n$—A—OH, whereby Z, n and A are as defined above, by reaction with the appropriate alcohol $R^9OH$, $R^{10}OH$ or carboxylic acid $R^{10}COOH$, respectively, to the formation of a compound of formula I containing a radical $R^1$, $R^2$, $R^3$ and/or $R^4$ which is either of the ester groups $(Z)_n$—A—$COOR^9$, $COOR^{10}$ or $(Z)_n$—A—$OCOR^{10}$.

The esterification is carried out as an ordinary esterification, in the presence of an acid catalyst such as sulfuric acid, hydrochloric acid and p-toluenesulphonic acid and, if necessary, in the presence of an inert solvent such as toluene.

(d) Acylation of a compound of the formula

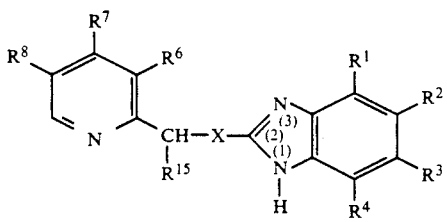

V wherein $R^{15}$, X, $R^1$, $R^2$, $R^3$, $R^4$, $R^6$, $R^7$ and $R^8$ are as defined above, by reaction with an appropriate acylating agent $(R^{14}CO)_2O$, $R^{14}COX^1$, whereby $X^1$ is a leaving group such as Cl, $N_3$ and p-nitrophenoxy, $R^aNCO$, whereby $R^a$ is defined by the relation $R^aNH$ equals $R^{14}$, provided that $R^a$ is K when $R^{14}$ is amino, to the formation of a compound of formula I wherein $R^5$ is $R^{14}CO$ as defined above.

The acylation is preferably carried out in the presence of a base such as triethylamine, $K_2CO_3$ and NaOH and with a solvent such as tetrahydrofuran acetonitrile and water. Normally, if the benzimidazole moiety is asymetrically substituted, both the N(1)- and the N(3)-acyl derivatives are obtained, and therefore, if necessary, the two components have to be separated. This may be done by recrystallizations or by extractive or chromatographic techniques.

(e) Hydrolyzing a compound of the formula

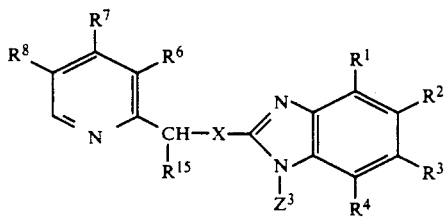

VI wherein X, $R^{15}$, $R^1$, $R^2$, $R^3$, $R^4$, $R^6$, $R^7$ and $R^8$ are as defined above and $Z^3$ is a suitable N-protecting group such as alkanyl, carboalkoxy and trimethylsilyl, to the formation of a compound of the formula I wherein $R^5$ is H.

The alkanoyl group in $Z^3$ can have 1-6 carbon atoms and the carboalkoxy group 2-6 carbon atoms. The hydrolysis may be performed in alkaline solution or in acidic solution, the latter mainly for compounds wherein X is S;

whereafter the compound of the formula I obtained if desired, when X is —S—, is converted to a physiologically acceptable salt or oxidized to form a compound of the formula I wherein X is —SO—.

Depending on the process conditions and the starting materials, the end products of the formula I wherein X is S is obtained either as the free base or as a salt. The end products of the formula I wherein X is —SO— are obtained as the free base. Both the free base and the salts of these end products are included within the scope of the invention. Thus, basic, neutral or mixed salts may be obtained as well as hemi, mono, sesqui or polyhydrates. Acid addition salts of the new sulfides may in a manner known per se be transformed into free base using basic agents such as alkali or by ion exchange. The free bases of the sulfides obtained may also form salts with organic or inorganic acids. In the preparation of acid addition salts preferably such acids are used which form suitable therapeutically acceptable salts.

Examples of such acids are hydrohalogen acids, sulfonic acid, phosphoric acid, nitric acid, and perchloric acid; aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, phenylacetic acid, benzoic acid, p-aminobenzoic acid, p-hydroxybenzoic acid, salicylic acid or p-aminosalicylic acid, embonic acid, methanesulfonic acid, ethanesulfonic acid, hydroxyethanesulfonic acid, ethylenesulfonic acid, halogenbenzenesulfonic acid, toluene-sulfonic acid, naphtylsulfonic acid or sulfanilic acids, methionine, tryptophane, lysine or arginine.

These or other salts of the new sulfide compounds, as e.g. picrates, may serve as purifying agents of the free bases obtained. Salts of the bases may be formed, separated from solution, and then the base can be recovered in higher purity from a new salt solution.

Racemates obtained can be separated according to known methods, e.g. recrystallization from an optically active solvent, use of microorganisms, reactions with optically active acids forming diastereomeric salts which can be separated, (e.g. separation based on different solubilities of the diastereomers), acylation of the benzimidazole nitrogen ($R^5$=H) or another nitrogen or oxygen atom in a substituent by an optically active activated carboxylic acid (e.g. acid chloride), followed by chromatographic separation and deacylation.

Suitable optically active acids for salt formation are the L- and D-forms of tartaric acid, di-o-tolyl-tartaric acid, malic acid, mandelic acid, camphorsulfonic acid or quinic acid, and for acylation O-methylmandelic acid. Preferably the more active part of the two antipodes is isolated.

In the case of diastereomeric mixtures (racemate mixtures) these may be separated into stereoisomeric (diastereomeric) pure racemates by means of chromatography or fractional crystallization.

The starting materials utilized in the processes a and c-e are obtained from the process b. The starting materials used for process b are in some cases known, but in most cases unknown. These unknown starting materials may, however, be obtained according to processes known per se.

Starting materials of the formula II

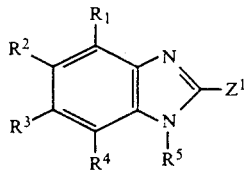

wherein $Z^1$ is SH may be obtained from the corresponding o-phenylenediamine by reaction with potassium ethylxanthate (Org. Synth. Vol. 30, p. 56) or thiophosgene.

The compounds of the formula II wherein $Z^1$ is alkylmercapto and alkylsulfinyl may be obtained from the above mentioned compound by simple S-alkylation with alkyl halide and by oxidation of the product from the S-alkylation, respectively.

The compounds of the formula II wherein $Z^1$ is halogen or acyloxy may be obtained from compounds of the same formula wherein $Z^1$ is OH by treatment with $POCl_3$, $POBr_3$ and the like or the appropriate acyl halide, respectively. The starting material wherein $Z^1$ is OH is obtained from the corresponding o-phenylenediamine by reaction with phosgene.

The o-phenylenediamines required may be obtained from the corresponding substituted benzenes according to processes known per se, e.g. by the consecutive processes: nitration, reduction, acetylation, nitration, deacetylation and reduction, or from one of the intermediary stages just mentioned. In order to obtain a o-phenylenediamine wherein $R^5$ is other than H, acylation (by the group $R^{14}CO$) is preferably made on the nitroaniline stage.

Starting materials of the formula

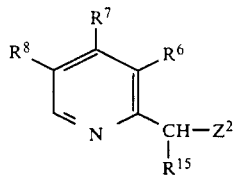

wherein $R^{15}$ is H, may be obtained either from the correspondingly substituted ($R^6$, $R^7$ and $R^8$) 2-methyl-substituted pyridene N-oxide via a known rearrangement to the intermediate 2-pyridinylmethanol or via a hydroxymethylation of the substituted ($R^6$, $R^7$ and $R^8$) pyridine to give the same intermediate, and then treatment of the 2-pyridinylmethanol with halogenating agents such as thionyl chloride or O-acylating agents such as p-toluenesulfonyl chloride to give compounds of the formula III wherein $Z^2$ is halogen and sulfonyloxy groups, respectively.

These leaving groups may then be substituted for alkyl-mercapto groups by treatment with e.g. sodium alkylmercaptide. which may then be oxidized to an alkylsulfinyl group, or substituted for SH by treatment with e.g. NaSH.

For the preparation of intermediates of formula

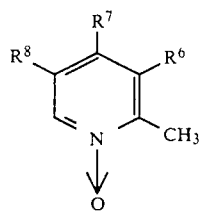

wherein $R^7$ is alkoxy, alkenyloxy, alkynyloxy, alkoxyalkoxy and dialkylaminoalkoxy, a compound of formula VII, wherein $R^7$ is $NO_2$, is reacted by the corresponding sodium alkoxide. Analogously, for the preparation of an intermediate of formula VII wherein $R^6$ and $R^7$ or $R^7$ and $R^8$ form a ring structure including an oxygen atom at position 4, a compound of formula VII wherein $R^7$ is $NO_2$ and $R^6$ or $R^8$ represents hyroxyalkyl is reacted with a non-nucleophilic base.

The following intermediates A) and B) are included in the scope of the invention:

A) New compounds of the formula

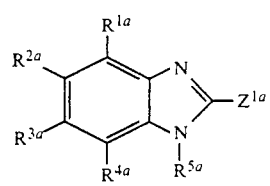

wherein $R^{1a}$, $R^{2a}$, $R^{3a}$ and $R^{4a}$ arethe same or different and selected from the groups
(a) H,
(b) alkyl containing 1-6 carbon atoms, including cycloalkyl,
(c) alkoxyalkyl containing 1-3 carbon atoms in the alkoxy part and 1-6 carbon atoms in the alkyl part,
(d) aryloxyalkyl containing 1-6 carbon atoms in the alkyl part,
(e) arylalkyl containing 1-6 carbon atoms in the alkyl part,
(f) aryl,
(g) alkoxy containing 1-6 carbon atoms,
(h) alkoxyalkoxy containing 1-3 carbon atoms in the outer part and 1-6 carbon atoms in the part nearest the aromatic ring,
(i) aryloxyalkoxy containing 1-6 carbon atoms in the alkoxy part,
(j) arylalkoxy containing 1-6 carbon atoms in the alkoxy part and
(k) aryloxy,
$R^{5a}$ is
(a) H,
(b) alkoxycarbonyl containing 1-4 carbon atoms in the alkoxy part,
(c) arylalkoxycarbonyl containing 1-2 carbon atoms in the alkoxy part,
(d) dialkylaminocarbonyl containing 1-4 carbon atoms in each alkyl group, or
(e) arylaminocarbonyl,
and $Z^{1a}$ is
(a) SH,
(b) Cl or Br
and provided that not more than one of $R^{1a}$, $R^{2a}$, $R^{3a}$ and $R^{4a}$ is H, are suitable intermediates for the preparation of compounds of the formula I with $R^1$, $R^2$, $R^3$, $R^4$ and $R^5$ having the same meaning as $R^{1a}$, $R^{2a}$, $R^{3a}$, $R^{4a}$ and $R^{5a}$, respectively, according to method b.

B) New compounds of the formula

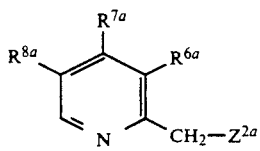   IX wherein $R^{6a}$ and $R^{8a}$ are
(a) H or
(b) alkyl containing 1–5 carbon atoms, and
$R^{7a}$ is
(a) alkenyloxy containing 2–5 carbon atoms, or
(b) alkynyloxy containing 2–5 carbon atoms,
(c) oxacycloalkyl containing one oxygen atom and 3–7 carbon atoms
(d) oxacycloalkoxy containing two oxygen atoms and 4–7 carbon atoms
(e) oxacycloalkylalkyl containing one oxygen atom and 4–7 carbon atoms
(f) oxacycloalkylalkoxy containing two oxygen atoms and 4–6 carbon atoms, or
(g) $R^{6a}$ and $R^{7a}$, or $R^{7a}$ and $R^{8a}$ together with the adjacent carbon atoms in the pyridine ring form a ring wherein the part constituted by $R^{6a}$ and $R^{7a}$ or $R^{7a}$ and $R^{8a}$ is

—CH=CH—CH=CH—

—O—(CH$_2$)$_{pa}$—

—CH$_2$—(CH$_2$)$_{pa}$—

—O—CH=CH— wherein PA is 2, 3 or 4 and the O atom always is attached to position $R^{7a}$,
and $Z^{2a}$ is
(a) SH,
(b) halogen Cl, Br, I cr
(c) OH
and provided that not more than one of $R^{6a}$ and $R^{8a}$ is H, are suitable intermediates for the preparation of compounds of the formula I with $R^6$, $R^7$ and $R^8$ having the same meaning as $R^{6a}$, $R^{7a}$ and $R^{8a}$, respectively, according to method b.

For clinical use the compounds of the invention are formulated into pharmaceutical formulations for oral, rectal, parenteral or other mode of administraction. The pharmaceutical formulation contains a compound of the invention in combination with a pharmaceutically acceptable carrier. The carrier may be in the form of a solid, semi-solid or liquid diluent, or a capsule. These pharmaceutical preparations are a further object of the invention. Usually the amount of active compounds is between 0.1–95% by weight of the preparation, between 0.2–20% by weight in preparations for parenteral use and between 1 and 50% by weight in preparations for oral administration.

In the preparation of pharmaceutical formulations containing a compound of the present invention in the form of dosage units for oral administration the compound selected may be mixed with a solid, powdered carrier, such as lactose, saccharose, sorbitol, mannitol, starch, amylopectin, cellulose derivatives, gelatin, or another suitable carrier, as well as with lubricating agents such as magnesium stearate, calcium stearate, sodium steryl fumarate and polyethylene glycol waxes. The mixture is then processed into granules or pressed into tablets. Since the sulfoxides of the invention are susceptible to degradation in acid to neutral media, granules and tablets containing sulfoxides are preferably coated with an enteric coating which protects the active compound from acid degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropylmethylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

Soft gelatine capsules may be prepared with capsules containing a mixture of the active compound or compounds of the invention, vegetable oil, fat, or other suitable vehicle for soft gelatine capsules. Soft gelatine capsules may also be enteric coated as described above. Hard gelatine capsules may contain granules or enteric-coated granules of the active compound. Hard gelatine capsules may also contain the active compound in combination with a solid powdered carrier such as lactose, saccharose, sorbitol, mannitol, potato starch, corn starch, amylopectin, cellulose derivatives or gelatine. The hard gelatine capsules may be enteric coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may by prepared in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugaralcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to be reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 500 mg per day of active substance.

The invention is illustrated by the following examples.

EXAMPLE 1

Method a. Preparation of 4,6-dimethyl-5-methoxy-2-[[(3,4-dimethyl-2-pyridinyl)methyl]sulfinyl]-1H-benzimidazole m-Chloroperbenzoic acid, 91% (0.53 g, 0.0028 mol) dissolved in $CH_2Cl_2$ (25 ml) and cooled to $-10°$ C. was added under stirring to 4,6-dimethyl-5-methoxy-2-[[(3,4-dimethyl-2-pyridinyl)methyl]thio]-1H-benzimidazole (0.91 g, 0.0028 mol) dissolved in $CH_2Cl_2$ (50 ml) maintaining the temperature at $-5°$ C. Stirring was continued at $-5°$ C. for 5 min and then NaOH (0.34 g, 0.0085 mol) dissolved in water (25 ml) was added under vigorous stirring. The two phases were separated and the aqueous phase was washed with $CH_2Cl_2$ (10 ml). More $CH_2Cl_2$ (50 ml) was added to the aqueous phase, the pH was adjusted to 9.5 by adding 2M HCl and after stirring the phases were separated. The organic phase was dried ($Na_2SO_4$), filtered and the solvent was evaporated off giving an oil which was crystallized from $CH_3CN$ (15 ml) yielding the desired product (0.3 g, 32%), m.p. 161° C.

EXAMPLE 2

Method a

Preparation of 4,6-dimethyl-5-heptyloxy-2-[[(4-methoxy-3,5-dimethyl-2-pyridinyl)methyl]sulfinyl]-1H-benzimidazole m-Chloroperbenzoic acid, 91% (1.13 g, 0.0059 mol) dissolved in $CH_2Cl_2$ (25 ml) and cooled to $-10°$ C. was added under stirring to 4,6-dimethyl-5-heptyloxy-2-[[(4-methoxy-3,5-dimethyl-2-pyridinyl)methyl]thio]-1H-benzimidazole (2.7 g, 0.0059 mol) dissolved in $CH_2Cl_2$ (50 ml) maintaining the temperature at $-5°$ C. Stirring was continued at $-5°$ C. for 10 min. The two phases were separated and then NaOH (0.26 g, 0.0066 mol) dissolved in water (50 ml) was added under vigorous stirring. The two phases were separated. The organic phase was dried ($Na_2SO_4$), filtered and the solvent evaporated off giving a residual oil, which according to NMR included 30% of unreacted starting material. The oil was chromatographed on a silica column using $CH_3OH$—$CH_2Cl_2$ 5:95 as eluant and then the product was recrystallized from $CH_3CN$ giving the desired product in crystalline form (0.85 g, 32%), m.p. 116° C.

Which one of these two procedures that have been used for the preparation of the different sulfoxides have been indicated in Table 2 below. For most of the compounds synthesized according to example 2 the chromatographic separation was not performed.

EXAMPLE 3

Method b

Preparation of 4,6-dimethyl-5-methoxy-2-[[(3,4-dimethyl-2-pyridinyl)methyl]thio]-1H-benzimidazole To 4,6-dimethyl-5-methoxy-2-mercapto-1H-benzimidazole (1.04 g, 0.0050 mol) in methanol (50 ml) were added (in the following order) NaOH (0.2 g, 0.0050 mol) dissolved in water (2 ml) and 3,4-dimethyl-2-chloromethylpyridine hydrochloride (0.96 g, 0.0050 mol). The mixture was heated until reflux. NaOH (0.2 g, 0.0050 mol) dissolved in water (2 ml) was added dropwise and then the reflux was continued for 3 hours. The mixture was poured on ice-water (200 ml). Filtration and recrystallization from $CH_3CN$ gave the desired product (1.1 g, 67%). NMR data for the final product is given below.

EXAMPLE 4 and 5

Method d. Preparation of $N^1$-benzoyl-5-methoxy-2-[[(4-methoxy-3,5-dimethyl-2-pyridinyl)methyl]thio]-1H-benzimidazole and $N^1$-benzoyl-6-methoxy-2-[[(4-methoxy-3,5-dimethyl-2-pyridinyl)methyl]thio]-1H-benzimidazole 5-Methoxy-2-[[(4-methoxy-3,5-dimethyl-2-pyridinyl)methyl]thio]-1H-benzimidazole (3.0 g, 0.009 mol) was dissolved in $CH_3CN$ (30 ml) and triethylamine (1.9 ml) was added. Benzoyl chloride (1.4 g, 0.010 mol) was added dropwise under stirring during 15 min. Then the mixture was stirred at 55° C. for 45 min. The solvent was evaporated off and ether was added to the residue under ice-cooling. The crystalline residue, thus obtained was stirred with water, filtered off and dried giving a white crystalline product mixture (1.9 g, 48%) of the desired two products in a 75:25 molar ratio (according to HPLC-analysis and NMR). NMR data for the final products is given below.

EXAMPLE 6

Method d

Preparation of N-methoxycarbonyl-5,6-methylenedioxy-2-[[(4-methoxy-3,5-dimethyl-2-pyridinyl)methyl]sulfinyl]-1H-benzimidazole Chloro methylformate (0.24 g, 0.0026 mol) dissolved in $CH_2Cl_2$ (5 ml) was added dropwise to a stirred solution of 5,6-methylenedioxy-2-[[(4-methoxy-3,5-dimethyl-2-pyridinyl)methyl]sulfinyl]-1H-benzimidazole (0.80 g, 0.0022 mol) and triethylamine in $CH_2Cl_2$ (10 ml). The mixture was then stirred at room temperature for 19 h. The $CH_2Cl_2$-solution was washed with water, dried ($MgSO_4$) and the solvent was evaporated giving the desired product as an oil (0.06 g, 6%). NMR data for the final product is given below.

EXAMPLE 7

Method d. Preparation of $N^1$-(N'-phenylcarbamoyl)-5,6-methylenedioxy-2-[[(4-methoxy-3,5-dimethyl-2-pyridinyl)methyl]sulfinyl]-1H-benzimidazole Phenylisocyanate (0.20 g, 0.00167 mol) dissolved in $CH_2Cl_2$ (5 ml) was added dropwise under stirring to a solution of 5,6-methylenedioxy-2-[[(4-methoxy-3,5-dimethyl-2-pyridinyl)methyl]sulfinyl]-1H-benzimidazole (0.50 g, 0.00139 mol) and triethylamine (0.28 g, 0.00278 mol) in $CH_2CL_2$ (15 ml). The mixture was then stirred at room temperature for 50 hours. The $CH_2Cl_2$-solution was washed with water, dried ($MgSO_4$) and the solvent was evaporated giving the desired product as an oil (0.03 g, 5%). NMR data for the final product is given below.

EXAMPLE 8

Method e

Preparation of
4,6-dimethyl-5-methoxy-2-[[(4-methoxy-3,5-dimethyl-2-pyridinyl)methyl]sulfinyl]-1H-benzimidazole.

$N^1$-Propionyl-4,6-dimethyl-5-methoxy-2-[[(4-methoxy-3,5-dimethyl-2-pyridinyl) methyl]sulfinyl]-1H-benzimidazole (1.0 g, 0.0023 mol) was heated in 1M NaOH (15 ml) for 1 h under stirring and $N_2$-atmosphere. pH was adjusted to 9.5 by addition of 2M HCl. Extraction with $CH_2Cl_2$, separation of the phases, drying the organic phase, evaporation of the solvent and recrystallization from $CH_3CN$ gave the desired product (0.30 g, 35%), m.p. 137° C.

The following Table 2 gives data for further examples of compounds of the invention.

TABLE 2

Summary of working examples.

| Ex | X | R15 | R1 | R2 | R3 | R4 | R5 | R6 | R7 | R8 | Method (Ex No.) | Yield % | M.p. (°C.) other data |
|---|---|---|---|---|---|---|---|---|---|---|---|---|---|
| 9 | S | H | CH3 | CH3 | CH3 | CH3 | H | CH3 | OCH2CH=CH2 | CH3 | b (Ex 3) | 82 | 164-165 |
| 10 | SO | H | CH3 | CH3 | CH3 | CH3 | H | CH3 | OCH2CH=CH2 | CH3 | a (Ex 2) | 73 | 146-148 |
| 11 | S | H | CH3 | CH3 | CH3 | CH3 | H | CH3 | OCH3 | CH3 | b (Ex 3) | 79 | 207 |
| 12 | SO | H | CH3 | CH3 | CH3 | CH3 | H | CH3 | OCH3 | CH3 | a (Ex 2) | 32 | 193 |
| 13 | S | H | CH3 | CH3 | CH3 | H | H | CH3 | OCH2CH=CH2 | CH3 | b (Ex 3) | 97 | 165 |
| 14 | SO | H | CH3 | CH3 | CH3 | H | H | CH3 | OCH2CH=CH2 | CH3 | a (Ex 2) | 59 | 147 |
| 15 | S | H | CH3 | CH3 | CH3 | H | H | CH3 | OCH3 | CH3 | b (Ex 3) | 79 | 159 |
| 16 | SO | H | CH3 | CH3 | CH3 | H | H | CH3 | OCH3 | CH3 | a (Ex 1) | 83 | 188 |
| 17 | S | H | CH3 | CH3 | H | CH3 | H | CH3 | OCH2CH=CH2 | CH3 | b (Ex 3) | 77 | NMR |
| 18 | SO | H | CH3 | CH3 | H | CH3 | H | CH3 | OCH2CH=CH2 | CH3 | a (Ex 1) | 58 | 129 |
| 19 | S | H | CH3 | CH3 | H | CH3 | H | CH3 | OCH3 | CH3 | b (Ex 3) | 79 | 163 |
| 20 | SO | H | CH3 | CH3 | H | CH3 | H | CH3 | OCH3 | CH3 | a (Ex 1) | 52 | 191 |
| 21 | S | H | CH3 | CH3 | H | H | H | CH3 | OCH2CH=CH2 | CH3 | b (Ex 3) | 37 | 109 |
| 22 | SO | H | CH3 | CH3 | H | H | H | CH3 | OCH2CH=CH2 | CH3 | a (Ex 1) | 58 | 149 |
| 23 | S | H | CH3 | CH3 | H | H | H | CH3 | OCH3 | CH3 | b (Ex 3) | 99 | 181 |
| 24 | SO | H | CH3 | H | CH3 | CH3 | H | CH3 | OCH2CH=CH2 | CH3 | a (Ex 1) | 71 | 157 |
| 25 | S | H | CH3 | H | CH3 | CH3 | H | CH3 | OCH2CH=CH2 | CH3 | b (Ex 3) | 62 | NMR |
| 26 | SO | H | CH3 | H | CH3 | H | H | CH3 | OCH2CH=CH2 | CH3 | a (Ex 1) | 10 | 155 |
| 27 | S | H | H | CH3 | H | H | H | CH3 | OCH2CH=CH2 | CH3 | b (Ex 3) | 90 | NMR |
| 28 | SO | H | H | CH3 | H | H | H | CH3 | OCH2CH=CH2 | CH3 | a (Ex 1) | 69 | 142 |
| 29 | S | H | H | OCH3 | H | H | H | CH3 | OCH2CH=CH2 | CH3 | b (Ex 3) | 74 | NMR |
| 30 | SO | H | H | OCH3 | H | H | H | CH3 | OCH2CH=CH2 | CH3 | a (Ex 1) | 55 | 134 |
| 31 | S | H | H | OCH3 | H | H | H | CH3 | OCH2CH=CH2 | CH3 | b (Ex 3) | 51 | 105-107 |
| 32 | SO | H | H | OCH3 | H | H | H | CH3 | OCH2CH=CH2 | CH3 | a (Ex 1) | 62 | 111 |
| 33 | S | H | H | OCH3 | H | H | H | CH3 | OCH2C≡CH | CH3 | b (Ex 3) | 66 | 154 |
| 34 | SO | H | H | OCH3 | H | H | H | CH3 | OCH2C≡CH | CH3 | a (Ex 1) | 71 | 145 |
| 35 | S | H | H | OCH3 | H | H | H | CH3 | OCH3 | C2H5 | b (Ex 3) | 31 | 147 |
| 36 | S | H | H | OCH3 | H | H | H | H | —(CH2)4— | CH3 | b (Ex 3) | 61 | NMR |
| 37 | SO | H | H | OCH3 | H | H | H | H | —(CH2)4— | CH3 | a (Ex 2) | 34 | NMR |
| 38 | S | H | H | O-CH-O (dioxole) | H | H | H | CH3 | OCH3 | CH3 | b (Ex 3) | 22 | 148 |
| 40 | S | H | CH3 | H | CH3 | H | H | CH3 | OCH2CH=CH2 | CH3 | b (Ex 3) | 76 | 134-136 |
| 41 | SO | H | CH3 | H | CH3 | H | H | CH3 | OCH2CH=CH2 | CH3 | a (Ex 1) | 35 | 111 |

TABLE 2-continued
Summary of working examples.

| Ex | X | R$^{15}$ | R$^1$ | R$^2$ | R$^3$ | R$^4$ | R$^5$ | R$^6$ | R$^7$ | R$^8$ | Method (Ex. No.) | Yield % | M.p. (°C.) other data |
|---|---|---|---|---|---|---|---|---|---|---|---|---|---|
| 42 | S | H | H | OCH$_2$CN | H | H | H | CH$_3$ | OCH$_3$ | CH$_3$ | b (Ex 3) | 29 | 66 |
| 43 | SO | H | H | OCH$_2$CN | H | H | H | CH$_3$ | OCH$_3$ | CH$_3$ | a (Ex 1) | 39 | 94 |
| 44 | S | H | H | (cyclohexyl) | H | H | H | CH$_3$ | OCH$_3$ | CH$_3$ | b (Ex 3) | 75 | NMR |
| 45 | SO | H | H | (cyclohexyl) | H | H | H | CH$_3$ | OCH$_3$ | CH$_3$ | a (Ex 2) | 60 | 155 |
| 47 | SO | H | H | COOCH$_2$CH$_2$OCH$_3$ | CH$_3$ | H | H | CH$_3$ | OCH$_3$ | CH$_3$ | a | | |
| 48 | S | H | H | COOCH$_2$-phenyl | CH$_3$ | H | H | CH$_3$ | OCH$_3$ | CH$_3$ | c | | |
| 49 | SO | H | H | COOCH$_2$-phenyl | CH$_3$ | H | H | CH$_3$ | OCH$_3$ | CH$_3$ | a | | |
| 50 | S | H | H | CH$_2$OH | CH$_3$ | H | H | CH$_3$ | OCH$_3$ | CH$_3$ | b (Ex 3) | 86 | 192 |
| 51 | SO | H | H | CH$_2$OH | CH$_3$ | H | H | CH$_3$ | OCH$_3$ | CH$_3$ | a (Ex 1) | 10 | 169 |
| 52 | S | H | H | CH$_2$OCO-phenyl | CH$_3$ | H | H | CH$_3$ | OCH$_3$ | CH$_3$ | c | | |

TABLE 2-continued

Summary of working examples.

| Ex | X | R15 | R1 | R2 | R3 | R4 | R5 | R6 | R7 | R8 | Method (Ex. No.) | Yield % | M.p. (°C.) other data |
|---|---|---|---|---|---|---|---|---|---|---|---|---|---|
| 53 | SO | H | H | CH₂OCO-⌬ | CH₃ | H | H | CH₃ | OCH₃ | CH₃ | a | 75 | 168 |
| 54 | S | H | H | COOCH₃ | CH₃ | H | H | CH₃ | OCH₂CH=CH₂ | CH₃ | b (Ex 3) | 52 | 139 |
| 55 | SO | H | H | COOCH₃ | CH₃ | H | H | CH₃ | OCH₂CH=CH₂ | CH₃ | a (Ex 1) | 70 | NMR |
| 56 | S | H | CH₃ | OCH₃ | CH₃ | H | H | CH₃ | OCH₃ | CH₃ | b (Ex 3) | 56 | 137 |
| 8 | SO | H | CH₃ | OCH₃ | CH₃ | H | H | CH₃ | OCH₃ | CH₃ | (Ex 1) / (Ex 8) | 35 | 137 |
| 3 | S | H | CH₃ | OCH₃ | CH₃ | H | H | CH₃ | CH₃ | H | b (Ex 3) | 67 | NMR |
| 1 | SO | H | CH₃ | OCH₃ | CH₃ | H | H | CH₃ | CH₃ | H | a (Ex 1) | 32 | 161 |
| 57 | S | H | CH₃ | OCH₂CH₂OCH₃ | CH₃ | H | H | CH₃ | OCH₃ | CH₃ | b (Ex 3) | 90 | NMR |
| 58 | SO | H | CH₃ | OCH₂CH₂OCH₃ | CH₃ | H | H | CH₃ | OCH₃ | CH₃ | a (Ex 1) | 68 | 144 |
| 59 | S | H | CH₃ | OCH₂CH₂OCH₃ | CH₃ | H | H | CH₃ | OCH₃ | CH₃ | b (Ex 3) | 95 | NMR |
| 60 | SO | H | CH₃ | OCH₂CH₂OCH₃ | CH₃ | H | H | CH₃ | OCH₃ | CH₃ | a (Ex 1) | 58 | 131 |
| 61 | S | H | CH₃ | COCH₃ | CH₃ | H | H | CH₃ | OCH₃ | CH₃ | b (Ex 3) | 90 | 192–4 |
| 62 | SO | H | CH₃ | COCH₃ | CH₃ | H | H | CH₃ | OCH₃ | CH₃ | a (Ex 2) | 25 | 164–5 |
| 63 | S | H | CH₃ | COCH₃ | CH₃ | H | H | H | H | CH₃ | b (Ex 3) | 99 | 184–6 |
| 64 | SO | H | CH₃ | COCH₃ | CH₃ | H | H | H | H | CH₃ | a (Ex 2) | 91 | 148–50 |
| 65 | S | H | CH₃ | COC₂H₅ | CH₃ | H | H | CH₃ | OCH₃ | CH₃ | b (Ex 3) | 68 | 149 |
| 66 | SO | H | CH₃ | COC₂H₅ | CH₃ | H | H | CH₃ | OCH₃ | CH₃ | a (Ex 2) | 48 | NMR |
| 67 | S | H | CH₃ | C₂H₅ | CH₃ | H | H | CH₃ | OCH₃ | CH₃ | b (Ex 3) | 91 | 182 |
| 68 | SO | H | CH₃ | C₂H₅ | CH₃ | H | H | CH₃ | OCH₃ | CH₃ | a (Ex 2) | 67 | 175–7 |
| 69 | S | H | CH₃ | C₂H₅ | CH₃ | H | H | H | OCH₃ | H | b (Ex 3) | 95 | NMR |
| 70 | SO | H | C₂H₅ | C₂H₅ | CH₃ | H | H | CH₃ | OCH₃ | H | a (Ex 2) | 73 | 142–3 |
| 71 | S | H | C₂H₅ | CN | C₂H₅ | H | H | CH₃ | OCH₃ | CH₃ | b (Ex 3) | 82 | 150 |
| 72 | SO | H | C₂H₅ | CN | C₂H₅ | H | H | CH₃ | OCH₃ | CH₃ | a (Ex 2) | 81 | 180 |
| 73 | S | H | CH₃ | OCH₃ | CH₃ | CH₃ | H | CH₃ | OCH₃ | CH₃ | b (Ex 3) | 82 | 143 |
| 74 | SO | H | CH₃ | OCH₃ | Cl | H | H | OH | OCH₃ | CH₃ | a (Ex 2) | 43 | 163 |
| 75 | S | H | Cl | Cl | Cl | H | H | CH₃ | OCH₃ | CH₃ | b (Ex 3) | 90 | 204 |
| 76 | SO | H | Cl | Cl | Cl | H | H | CH₃ | OCH₃ | CH₃ | a | | |
| 77 | SO | H | H | CH₃ | CH₃ | H | H | H | OCH₃ | C₂H₅ | a (Ex 1) | 43 | 156 |

TABLE 2-continued

Summary of working examples.

[Structure diagram showing benzimidazole-pyridine compound with substituents R¹-R⁸, R¹⁵, and X linker]

| Ex | X | R¹⁵ | R¹ | R² | R³ | R⁴ | R⁵ | R⁶ | R⁷ | R⁸ | Method (Ex. No.) | Yield % | M.p. (°C.) other data |
|---|---|---|---|---|---|---|---|---|---|---|---|---|---|
| 78 | S | H | H | CH₃ / piperidyl-CON | H | H | H | CH₃ | OCH₃ | CH₃ | b (Ex 3) | 90 | NMR |
| 79 | SO | H | H | CH₃ / piperidyl-CON | H | H | H | CH₃ | OCH₃ | CH₃ | a (Ex 1) | 61 | NMR |
| 80 | S | H | H | —OCH₂O— | | H | H | CH₃ | OCH₃ | CH₃ | b (Ex 3) | 91 | 168 |
| 81 | SO | H | H | —OCH₂O— | | H | H | CH₃ | OCH₃ | CH₃ | a (Ex 1) | 67 | 165 |
| 82 | S | H | —CH=CH—CH=CH— | | | H | H | CH₃ | OCH₃ | CH₃ | b (Ex 3) | 73 | NMR |
| 83 | SO | H | —CH=CH—CH=CH— | | | H | H | CH₃ | OCH₃ | CH₃ | a (Ex 1) | 60 | 184 |
| 84 | S | H | H | —CH=CH—CH=CH— | | H | H | CH₃ | OCH₃ | CH₃ | b (Ex 3) | 78 | 191 |
| 85 | SO | H | H | —CH=CH—CH=CH— | | H | H | CH₃ | OCH₃ | CH₃ | a (Ex 1) | 34 | 175 |
| 86 | S | H | H | —CH₂CH₂CH₂CH₂— | | H | H | CH₃ | OCH₃ | CH₃ | b (Ex 3) | 58 | NMR |
| 87 | SO | H | H | —CH₂CH₂CH₂CH₂— | | H | H | CH₃ | OCH₃ | CH₃ | a (Ex 1) | 27 | 175 |
| 88 | S | H | H | —OCH₂O— | | H | CO₂CH₃ | CH₃ | OCH₃ | CH₃ | d | 6 | |
| 6 | SO | H | H | —OCH₂O— | | H | CO₂CH₃ | CH₃ | OCH₃ | CH₃ | d (Ex 6) | 5 | NMR |
| 7 | SO | H | H | —OCH₂O— | | H | Ph-CONH | CH₃ | OCH₃ | CH₃ | d (Ex 7) | | NMR |
| 90 | S | H | H | Ph-OCH₂CH₂CH₂O | H | H | H | CH₃ | OCH₃ | CH₃ | b (Ex 3) | 25 | NMR |

TABLE 2-continued
Summary of working examples.

| Ex | X | R15 | R1 | R2 | R3 | R4 | R5 | R6 | R7 | R8 | Method (Ex. No.) | Yield % | M.p. (°C.) other data |
|---|---|---|---|---|---|---|---|---|---|---|---|---|---|
| 91 | SO | H | H | OCH2CH2CH2O— (phenyl) | | H | H | CH3 | OCH3 | CH3 | a (Ex 2) | 78 | 61 |
| 92 | S | H | CH3 | O(CH2)6CH3 | CH3 | H | H | CH3 | OCH3 | CH3 | b (Ex 3) | 64 | NMR |
| 2 | SO | H | CH3 | O(CH2)6CH3 | CH3 | H | H | CH3 | OCH3 | CH3 | a (Ex 2) | 32 | 116 |
| 93 | S | H | H | C2H5 | H | H | H | CH3 | OCH2CH=CH2 | CH3 | b (Ex 3) | 45 | NMR |
| 94 | SO | H | H | C2H5 | H | H | H | CH3 | OCH2CH=CH2 | CH3 | a (Ex 1) | 49 | 124-6 |
| 95 | S | H | H | OCH3 | H | H | H | CH3 | OCH2CH2CH(CH3)2 | CH3 | b (Ex 3) | 95 | NMR |
| 96 | SO | H | H | OCH3 | H | H | H | CH3 | OCH2CH2CH(CH3)2 | CH3 | a (Ex 1) | 33 | 111 |
| 97 | S | H | —CH=CH—CH=C—CH2CH2— | | | H | H | CH3 | OCH3 | CH3 | b (Ex 3) | 96 | 190 |
| 98 | SO | H | —CH=CH—CH=C—CH2CH2— | | | H | H | CH3 | OCH3 | CH3 | a (Ex 2) | 93 | 109 |
| 4 | S | H | H | OCH3 | H | H | (phenyl)CO | CH3 | OCH3 | CH3 | d (Ex 4) | 48 | NMR |
| 5 | S | H | H | H | OCH3 | H | (phenyl)CO | CH3 | OCH3 | CH3 | d (Ex 5) | | |
| 99 | S | H | H | CH(CH3)2 | H | H | H | CH3 | OCH3 | CH3 | b (Ex 3) | 99 | 70 |
| 101 | S | H | H | C(CH3)3 | H | H | H | CH3 | OCH3 | CH3 | a (Ex 2) | 52 | 88-89 |
| 102 | SO | H | H | C(CH3)3 | H | H | H | CH3 | OCH3 | CH3 | b (Ex 3) | 12 | NMR |
| 103 | S | H | H | CH2CH2OCH3 | H | H | H | CH3 | OCH3 | CH3 | b (Ex 3) | 84 | NMR |
| 104 | SO | H | H | CH2CH2OCH3 | H | H | H | CH3 | OCH3 | CH3 | a (Ex 1) | 38 | 118 |

TABLE 2-continued

Summary of working examples.

| Ex | X | R15 | R1 | R2 | R3 | R4 | R5 | R6 | R7 | R8 | Method (Ex. No.) | Yield % | M.p. (°C.) other data |
|---|---|---|---|---|---|---|---|---|---|---|---|---|---|
| 105 | S | H | H | (1,1-cyclohexanediyldioxy) | H | H | H | CH$_3$ | OCH$_3$ | CH$_3$ | b (Ex 3) | 58 | 216 |
| 106 | SO | H | H | (1,1-cyclohexanediyldioxy) | H | H | H | CH$_3$ | OCH$_3$ | CH$_3$ | a (Ex 2) | 32 | 158 |
| 107 | SO | H | H | OCH$_3$ | H | H | CO$_2$CH$_3$ | CH$_3$ | OCH$_3$ | CH$_3$ | d } (Ex 4 and 5) | } 6 | } NMR |
| 108 | SO | H | H | H | OCH$_3$ | H | CO$_2$CH$_3$ | CH$_3$ | OCH$_3$ | CH$_3$ | d | | 147–148 |
| 109 | S | H | H | SCH$_3$ | H | H | H | CH$_3$ | OCH$_3$ | CH$_3$ | b (Ex 3) | 83 | $^1$H NMR |
| 110 | S | H | H | CH(CH$_3$)$_2$ | H | H | H | CH$_3$ | OCH$_2$-(tetrahydrofuran-2-yl) | CH$_3$ | b (Ex 3) | 86 | $^1$H NMR |
| 111 | SO | H | H | CH(CH$_3$)$_2$ | H | H | H | CH$_3$ | OCH$_2$-(tetrahydrofuran-2-yl) | CH$_3$ | a (Ex 2) | 89 | $^1$H NMR |
| 112 | S | H | H | CH$_2$CH$_2$COCH$_3$ | H | H | H | CH$_3$ | OCH$_2$CH=CH$_2$ | CH$_3$ | b (Ex 3) | 40 | $^1$H NMR |
| 113 | SO | H | H | CH$_2$CH$_2$COCH$_3$ | H | H | H | CH$_3$ | OCH$_2$CH=CH$_2$ | CH$_3$ | a (Ex 2) | 28 | 123–4 |
| 114 | S | H | H | CHO | H | H | H | CH$_3$ | OCH$_3$ | CH$_3$ | b (Ex 3) | 21 | 162 |

TABLE 2-continued
Summary of working examples.

| Ex | X | R$^{15}$ | R$^1$ | R$^2$ | R$^3$ | R$^4$ | R$^5$ | R$^6$ | R$^7$ | R$^8$ | Method (Ex. No.) | Yield % | M.p. (°C.) other data |
|---|---|---|---|---|---|---|---|---|---|---|---|---|---|
| 115 | S | H | H | OCH$_3$ | H | H | H | —CH=CH—CH=CH— | | H | b (Ex 3) | 67 | 105 |
| 116 | SO | H | H | OCH$_3$ | H | H | H | —CH=CH—CH=CH— | | H | a (Ex 1) | 66 | 100 |
| 117 | S | H | H | -O-C$_6$H$_5$ | H | H | H | CH$_3$ | OCH$_3$ | CH$_3$ | b (Ex 3) | 98 | 122 |
| 118 | SO | H | H | -O-C$_6$H$_5$ | H | H | H | CH$_3$ | OCH$_3$ | CH$_3$ | a (Ex 2) | 80 | 118 |
| 119 | S | H | H | -OCH$_2$CH$_2$-C$_6$H$_5$ | H | H | H | CH$_3$ | OCH$_3$ | CH$_3$ | b (Ex 3) | 80 | $^1$H NMR |
| 120 | SO | H | H | -OCH$_2$CH$_2$-C$_6$H$_5$ | H | H | H | CH$_3$ | OCH$_3$ | CH$_3$ | a (Ex 2) | 55 | 145 d |
| 121 | S | H | H | -CO-C$_6$H$_5$ | H | H | H | CH$_3$ | OCH$_3$ | CH$_3$ | b (Ex 3) | 82 | $^1$H NMR |
| 122 | SO | H | H | -CO-C$_6$H$_5$ | H | H | H | CH$_3$ | OCH$_3$ | CH$_3$ | a (Ex 2) | 24 | $^1$H NMR |

TABLE 2-continued

Summary of working examples.

| Ex | X | R15 | R1 | R2 | R3 | R4 | R5 | R6 | R7 | R8 | Method (Ex. No.) | Yield % | M.p. (°C.) other data |
|---|---|---|---|---|---|---|---|---|---|---|---|---|---|
| 123 | S | H | H | (phenyl) | H | H | H | CH₃ | OCH₃ | CH₃ | b (Ex 3) | 88 | 158 |
| 124 | SO | H | H | (phenyl) | H | H | H | CH₃ | OCH₃ | CH₃ | a (Ex 2) | 52 | 104 |
| 125 | S | H | H | SOCH₃ | H | H | H | CH₃ | OCH₃ | CH₃ | b (Ex 3) | 57 | ¹H NMR |
| 126 | SO | H | H | SOCH₃ | H | H | H | CH₃ | OCH₃ | CH₃ | a (Ex 1) | 47 | ¹H NMR |
| 127 | SO | H | H | NO₂ | H | H | H | CH₃ | OCH₃ | CH₃ | b (Ex 1) | 14 | ¹H NMR |
| 128 | S | H | H | Br | H | H | H | CH₃ | OCH₂CH=CH₂ | CH₃ | b (Ex 3) | 64 | 171 |
| 129 | SO | H | H | Br | H | H | H | CH₃ | OCH₂CH=CH₂ | CH₃ | a (Ex 2) | 58 | 143 |
| 130 | S | H | H | OCH₃ | H | H | H | —CH=CH—O— | | H | b (Ex 3) | 77 | NMR |
| 131 | SO | H | H | OCH₃ | H | H | H | —CH=CH—O— | | H | a (Ex 2) | 19 | NMR |
| 132 | SO | H | H | CH₃ | CH₃ | H | O=COC(CH₃)₃ | CH₃ | OCH₃ | CH₃ | d (Ex 6) | 22 | 168 |
| 134 | SO | H | H | CH₃ | CH₃ | H | O=CN(CH₃)₂ | CH₃ | OCH₃ | CH₃ | d (Ex 6) | 21 | ¹H NMR |
| 135 | S | H | H | CH₃ | CH₃ | H | H | CH₃ | OCH₂(tetrahydrofuranyl) | CH₃ | | | |
| 136 | SO | H | H | CH₃ | CH₃ | H | H | CH₃ | OCH₂(tetrahydrofuranyl) | CH₃ | | | |

TABLE 2-continued

Summary of working examples.

structure: benzimidazole (with R1, R2, R3, R4, R5) connected via –CH(R15)–X– to pyridine (with R6, R7, R8)

| Ex | X | R15 | R1 | R2 | R3 | R4 | R5 | R6 | R7 | R8 | Method (Ex. No.) | Yield % | M.p. (°C.) other data |
|---|---|---|---|---|---|---|---|---|---|---|---|---|---|
| 137 | S | H | H | –CH2CH2CH2– | | H | H | CH3 | OCH3 | CH3 | b (Ex 3) | 74 | 160 |
| 138 | SO | H | H | –CH2CH2CH2– | | H | H | CH3 | OCH3 | CH3 | a (Ex 1) | 40 | 171 |
| 139 | S | H | H | –CH=CH–CH=N– | | H | H | CH3 | OCH3 | CH3 | b (Ex 3) | 38 | NMR |
| 140 | SO | H | H | –CH=CH–CH=N– | | H | H | CH3 | OCH3 | CH3 | a (Ex 1) | 26 | 60 |
| 141 | S | H | H | –OCH2O– | | H | H | CH3 | CH3 | CH3 | b (Ex 3) | 83 | 193–95 |
| 142 | SO | H | H | –OCH2O– | | H | H | CH3 | CH3 | CH3 | a (Ex 2) | 76 | 173 |
| 143 | SO | H | H | O=COCH3 | CH3 | H | H | H | OCH3 | C2H5 | a (Ex 2) | 49 | 154 |
| 144 | S | H | CH3 | CH3 | CH3 | H | H | CH3 | CH3 | H | b (Ex 3) | 39 | 1H NMR |
| 145 | SO | H | CH3 | CH3 | CH3 | H | H | CH3 | CH3 | H | a (Ex 2) | 65 | 1H NMR |
| 146 | S | H | CH3 | CH3 | CH3 | H | H | H | CH3 | CH3 | b (Ex 3) | 78 | 143 |
| 147 | SO | H | CH3 | CH3 | CH3 | H | H | H | CH3 | CH3 | a (Ex 2) | 64 | 180 |
| 148 | S | H | CH3 | CH3 | CH3 | CH3 | H | CH3 | H | CH3 | b (Ex 3) | 70 | 239–42 |
| 149 | SO | H | CH3 | CH3 | CH3 | CH3 | H | CH3 | H | CH3 | a (Ex 2) | 14 | 171 |
| 150 | S | H | CH3 | CH3 | H | H | H | CH3 | CH3 | H | b (Ex 3) | 96 | 210 |
| 151 | SO | H | CH3 | CH3 | H | H | H | CH3 | CH3 | H | a (Ex 2) | 66 | 1H NMR |
| 152 | S | H | CH3 | CN | CH3 | H | H | CH3 | OC2H5 | CH3 | b (Ex 3) | 94 | 151 |
| 153 | SO | H | CH3 | CN | CH3 | H | H | CH3 | OC2H5 | CH3 | 1 (Ex 2) | 29 | 150 |
| 154 | S | H | H | cyclohexyl | | H | H | H | CH3 | C2H5 | b (Ex 3) | 48 | 1H NMR |
| 155 | SO | H | H | cyclohexyl | | H | H | H | CH3 | C2H5 | a (Ex 2) | 44 | 105 |

TABLE 2-continued

Summary of working examples.

| Ex | X | $R^{15}$ | $R^1$ | $R^2$ | $R^3$ | $R^4$ | $R^5$ | $R^6$ | $R^7$ | $R^8$ | Method (Ex. No.) | Yield % | M.p. (°C.) other data |
|---|---|---|---|---|---|---|---|---|---|---|---|---|---|
| 156 | S | H | H | cyclohexyl | H | H | H | $CH_3$ | $OCH_2CH_2OCH_3$ | $CH_3$ | b (Ex 3) | 94 | $^1$H NMR |
| 157 | SO | H | H | cyclohexyl | H | H | H | $CH_3$ | $OCH_2CH_2OCH_3$ | $CH_3$ | a (Ex 2) | 18 | 181 |
| 158 | S | H | H | $CF_3$ | H | H | H | $CH_3$ | $OCH_2$-(tetrahydrofuran-2-yl) | $CH_3$ | b (Ex 3) | 67 | 100 |
| 159 | SO | H | H | $CF_3$ | H | H | H | $CH_3$ | $OCH_2$-(tetrahydrofuran-2-yl) | $CH_3$ | a (Ex 2) | 57 | 125 |
| 160 | S | H | H | $CH_2CH_2COOC_2H_5$ | H | H | $\overset{O}{\underset{\|}{C}}$—$OC(CH_3)_3$ | $CH_3$ | $OCH_3$ | $CH_3$ | b (Ex 3) | 15 | $^1$H NMR |
| 161 | SO | H | H | $OCH_3$ | H | H | H | $CH_3$ | $OCH_3$ | $CH_3$ | d (Ex 6) | 50 | 155 |
| 163 | SO | H | H | $OCH_3$ | H | H | H | H | —$CH_2CH_2O$—<br>—$CH_2CH_2CH_2O$— | H | b (Ex 3) | 71 | $^1$H NMR |
| 164 | SO | H | H | $OCH_3$ | H | H | H | H | | H | | | |
| 165 | SO | H | H | $OCH_3$ | H | H | H | H | —$OCH_2CH_2$—<br>—$OCH_2CH_2CH_2$— | H | | | |
| 166 | SO | H | H | $OCH_3$ | H | H | H | H | | H | | | |

| Example No. | Identifying data for compounds of the invention<br>¹H NMR-data of the compounds in Table 2 (90 MHz)<br>NMR-data: δ(CDCl₃) ppm |
|---|---|
| 17 | 2.3 (s,3H), 2.35(d,6H), 2.5(s,3H), 2.55(s,3H), 4.4(s,2H), 4.25–4.4(d,2H), 5.2–5.6(m,2H), 5.9–6.4(m,1H), 6.9(s,1H), 8.35(s,1H). |
| 27 | 2.2(s,3H), 2.3(s,3H), 2.6(s,3H), 4.35–4.45(d,2H), 4.45(s,2H), 5.2–5.6(m,2H), 5.85–6.35(m,1H), 6.9–7.55(m,3H), 8.3(s,1H). |
| 29 | 2.2(s,3H), 2.25(s,3H), 2.4(s,3H), 4.2–4.35(d,2H), 4.4(s,2H), 5.5–5.6(m,2H), 5.85–6.3(m,1H), 6.9–7.1(d,1H), 7.3–7.55(t,2H), 8.3(s,1H). |
| 36 | 1.8(m,4H), 2.75(m,4H), 3.8(s,3H), 4.25(s,2H), 6.85(m,1H), 7.05(s,2H), 7.4(d,1H), 8.3(s,1H). |
| 37 | 1.7(m,4H), 2.3–2.7(m,4H), 3.85(s,3H), 4.6(d,2H), 6.8(s,1H), 7.05(s,2H), 7.6(m,1H), 8.3(s,1H). |
| 44 | 1.2–4.0(m,10H), 2.25(s,3H), 2.3(s,3H), 2.6(m,1H), 3.75(s,3H), 4.45(s,2H), 7.1(q,1H), 7.5(m,2H), 8.35(s,1H). |
| 3 | 2.3(s,6H), 2.35(s,3H), 2.5(s,3H), 3.75(s,3H), 4.4(s,2H), 7.05–7.2(d,1H), 7.25(s,1H), 8.3–8.45(d,1H). |
| 57 | 2.2(s,3H), 2.25(s,3H), 2.3(s,3H), 2.5(s,3H), 3.45(s,3H), 3.75(s,3H), 3.85(m,4H), 4.3(s,2H), 7.2(br.s., 1H), 8.3(s,1H). |
| 59 | 2.3(s,6H), 2.4(s,3H), 2.55(s,3H), 3.5(s,3H), 3.9(m,4H), 4.3(s,2H), 7.2(s,1H), 7.3(s,1H), 8.4(s,1H), 9.3(br.s., 1H). |
| 66 | 1.2(t,3H), 2.15(s,3H), 2.2(s,3H), 2.3(s,3H), 2.4(s,3H), 2.8(q,2H), 3.65(s,3H), 4.8(s,2H), 7.3(s,1H), 8.25(s,1H). |
| 69 | 1.1(t,3H), 2.2(s,3H), 2.4(s,3H), 2.55(s,3H), 2.75(q,2H), 3.85(s,3H), 4.35(s,2H), 6.75(d,1H), 7.25(s,1H), 8.4(d,1H). |
| 78 | 1.2(d,3H), 1.6(m,6H), 2.25(s,3H), 2.3(s,3H), 3.0(m,1H), 3.75(s,3H), 4.15(m,1H), 4.45(s,2H), 4.55(m,1H), 7.3(q,1H), 7.6(m,2H), 8.3(s,1H). |
| 79 | 1.25(d,3H), 1.65(m,6H), 2.15(s,3H), 2.2(s,3H), 3.1(m,1H), 3.65(s,3H), 4.1(m,1H), 4.6(m,1H), 4.8(s,2H), 7.4(q,1H), 7.7(d,1H), 7.8(s,1H), 8.2(s,1H). |
| 82 | 2.2(s,3H), 2.3(s,3H), 3.7(s,3H), 4.75(s,2H), 7.3–8.5(m,8H). |
| 86 | 1.85(m,4H), 2.2(s,3H), 2.25(s,3H), 2.7–3.1(m,4H), 3.75(s,3H), 4.35(s,2H), 6.9(d,1H), 7.3(d,1H), 8.25(s,1H). |
| 6 | 2.2(s,3H), 2.35(s,3H), 3.8(s,3H), 4.15(s,3H), 4.75(s,2H), 6.1(s,2H), 7.3(s,1H), 7.5(s1H), 8.15(s,1H). |
| 7 | 2.15(s,3H), 2.2(s,3H), 3.7(s,3H), 4.7(s,2H), 6.05(s,2H), 7.0–7.6(m,7H), 8.15(s,1H), 8.3(s,1H). |
| 90 | 2.25(s,3H), 2.1–2.4(m,2H), 2.3(s,3H), 3.75(s,3H), 4.2(t,4H), 4.4(s,2H), 6.75–7.2(m,5H), 7.2–7.6(m,3H), 8.35(s,1H). |
| 92 | 0.7–2.05(m,13H), 2.25(s,3H), 2.3(s,3H), 2.35(s,3H), 2.5(s,3H), 3.65–3.9(m,2H), 3.75(s,3H), 4.35(s,2H), 7.2(s,1H), 8.3(s,1H). |
| 93 | 1.25(t,3H), 2.25(s,3H), 2.3(s,3H), 2.8(q,2H), 4.4(d,2H), 4.45(s,2H), 5.2–5.65(m,2H), 5.85–6.3(m,1H), 7.0–7.65(m,2H), 7.5(s,1H), 8.35(s,1H). |
| 95 | 0.9(s,3H), 1.0(s,3H), 1.5–1.95(m,2H), 2.15–2.45(m,1H), 2.25(s,3H), 2.3(s,3H), 3.7–4.0(t,2H), 3.85(s,3H), 4.45(s,2H), 2.8–7.0(m,1H), 7.15(d,1H), 7.45–7.55(d,1H), 8.3(s,1H). |
| 4 + 5 | 2.25(s,3H), 2.40(s,3H), 3.6 and 3.85(2s, total 3H), 3.80(s,3H), 4.8 and 4.85(2s,total 2H), 6.35–7.95(m,8H), 8.35(s,1H). |
| 103 | 2.3(s,3H), 2.35(s,3H), 3.0(t,2H), 3.35(s,3H), 3.65(t,2H), 3.8(s,3H), 4.4(s,2H), 6.8–7.6(m,4H), 8.25(s,1H). |
| 107 + 108 | 2.2(s,3H), 2.35(s,3H), 3.75(s,3H), 3.9 and 3.95 (2s,total 3H), 4.15(s,3H), 4.75(s,2H), 7.07–7.95 (m,3H), 8.15(s,1H). |
| 102 | 1.32(s,9H), 2.08(s,3H), 2.15(s,3H), 4.09(d,2H), 4.74(s,2H), 5.10–5.45(m,2H), 5.73–6.25(m,1H), 7.28–7.73(m,3H), 8.27(s,1H). |
| 139 | 2.22(s,3H), 2.29(s,3H), 3.75(s,3H), 4.40(s,2H), 7.38–7.58(m,1H), 7.87–8.02(m,2H), 8.29–8.47(m,1H), 8.70–9.00(m,2H). |
| 110 | 1.25(d,6H), 1.6–2.15(m,4H), 2.25(s,3H), 2.3(s,3H), 3.0(m,1H), 3.7–4.05(m,4H), 4.25(m,1H), 4.5(s,2H), 7.15(q,1H), 7.5(s,1H), 7.55(d,1H), 8.3(s,1H). |
| 111 | 1.3(d,6H), 1.55–2.15(m,4H), 2.2(s,3H), 2.25(s,3H), 3.05(m,1H), 3.65(d,2H), 3.9(m,2H), 4.2(m,1H), 4.8(s,2H), 7.3(d,1H), 7.4–7.8(m,2H), 8.3(s,1H). |
| 119 | 2.3(s,3H), 2.35(s,3H), 3.15(t,2H), 3.7(s,3H), 4.25(t,2H), 4.4(s,2H), 6.9(q,1H), 7.15(d,1H), 7.3–7.6(m,6H), 8.35(s,1H). |
| 125 | 2.3(s,3H), 2.35(s,3H), 2.8(s,3H), 3.8(s,3H), 4.5(s,2H), 7.5(d,1H), 7.75(d,1H), 8.05(s,1H), 8.4(s,1H). |
| 126 | 2.2(s,6H), 2.8(s,3H), 3.7(s,3H), 4.85(s,2H), 7.6(q,1H), 7.85(d,1H), 8.15(s,1H), 8.25(s,1H). |
| 127 | 2.25(d,6H), 3.75(s,3H), 4.9(d,2H), 7.8(d,1H), 8.3(s,1H), 8.3(q,1H), 8.65(d,1H). |
| 134 | 2.2(d,6H), 2.35(d,6H), 3.1(s,6H), 3.7(s,3H), 4.95(s,2H), 7.2(s,1H), 7.6(s,1H), 8.3(s,1H). |
| 112 | 2.1(s,3H), 2.25(s,3H), 2.3(s,3H), 2.65–3.2(m,4H), 4.4(d,2H), 4.42(s,2H), 5.2–5.6(m,2H), 5.9–6.4(m,1H), 7.1(dd,1H), 7.4(d,1H), 7.5(d,1H), 8.35(s,1H). |
| 121 | 2.25(s,3H), 2.35(s,3H), 3.8(s,3H), 4.45(s,2H), 7.45–8.0(m,7H), 8.15(s,1H), 8.4(s,1H). |
| 122 | 2.2(s,6H), 3.7(s,3H), 4.8(d,2H), 7.5–8.05(m,7H), 8.2(s,1H), 8.25(s,1H). |
| 144 | 2.25(s,3H), 2.35(s,6H), 2.38(s,3H), 2.55(s,3H), 4.4(s,2H), 7.15(d,1H), 7.3(s,1H), 8.4(d,1H). |
| 145 | 2.15(s,3H), 2.25(s,3H), 2.27(s,3H), 2.4(s,3H), 2.47(s,3H), 4.8(s,2H), 7.1(d,1H), 7.3(s,1H), 8.37(d,1H). |
| 151 | 2.2(s,3H), 2.23(s,3H), 2.35(s,3H), 2.4(s,3H), 2.47(s,3H), 4.8(d,2H), 7.0(s,1H), 7.1(d,1H), 8.37(d,1H). |
| 130 | 3.85(s,3H), 4.65(s,2H), 6.8–7.8(m,7H), 8.55(d,1H) |
| 131 | 3.85(s,3H), 4.95(d,2H), 6.65–7.60(m,7H), 8.45(d,1H). |
| 160 | 1.15(t,3H), 2.20(s,3H), 2.27(s,3H), 2.49–2.73(m,2H), 2.89–3.13(m,2H), 3.72(s,3H), 4.09(q,2H), 4.37(s,2H), 6.98 and 7.08(dd,1H), 7.30–7.55(m,2H), 8.28(s,1H). |
| 154 | 1.1–2.1(m,13H), 2.3(s,3H), 2.5–2.8(m,3H), 4.4(s,2H), 7.1–7.65(m,4H), 8.5(s,1H) |
| 156 | 1.1–2.0(m,11H), 2.25(s,3H), 2.3(s,3H), 3.45(s,3H), 3.7(t,2H), 4.0(t,2H), 4.4(s,2H), 7.05–7.65(m,3H), 8.35(s,1H) |
| 164 (270 MHz) | 2.13(m,2H), 2.88(t,2H), 3.82(s,3H), 4.26(t,2H), 4.69(s,2H), 6.7–6.85(m,2H), 7.04(d,1H), 7.39(d,1H), 8.1(d,1H). |

PREPARATION OF INTERMEDIATES

EXAMPLE 1

Method A

Preparation of 4,5,7-trimethyl-2-mercapto-1H-benzimidazole

2-Nitro-3,4,6-trimethylaniline (10.2 g, 0.057 mol) was dissolved in 95% ethanol (900 ml) and hydrogenated in the presence of Pd/C-catalyst until the theoretical amount of hydrogen had been consumed (1 hour). The whole mixture was transferred to another flask and potassium ethylxanthate (12.8 g, 0.080 mol) dissolved in water (12.5 ml) was added. The mixture was refluxed overnight, 2M NaOH (20 ml) was added and the volatiles were evaporated off. The residue was dissolved in methanol (300 ml) and the catalyst was filtered off. Part of the solvent (200 ml) was evaporated off. Water (100 ml) was added and the mixture was acidified with acetic acid (10 ml) dissolved in water (20 ml). The crystalline precipitate was filtered off, washed with water and dried under reduced pressure, giving the desired product (7.2 g, 66%), NMR: δ (CDCl₃) 2.0(s,3H), 2.05(s,3H), 2.1(s,3H), 3.3(br.s, 1H), 6.5(s,1H).

EXAMPLE 12

Method B

Preparation of 4,6,7-trimethyl-5-methoxy-2-mercapto-1H-benzimidazole

A solution of 4-methoxy-3,5,6-trimethyl-1,2-phenylenediamine (1.8 g, 0.010 mol) and triethylamine (2.1 g, 0.021 mol) in $CHCl_3$ (15 ml) was added dropwise to a stirred solution of thiophosgene (0.60 g, 0.0052 mol) in $CHCl_3$ (5 ml). The mixture was then stirred at room temperature for 1 hour. Water (15 ml) and triethylamine (0.5 g) was added and the mixture was stirred for 1 hour. The precipitate was filtered off, washed with water and dried in the air giving the desired product (0.96 g, 43%), NMR: δ ($CDCl_3$) 2.5 (s,3H), 2.65(s,6H), 3.65(s,3H), 12.0(br.s.,1H).

Example 13 Method C. Preparation of 4-allyloxy-3,5-dimethyl-2-pyridinyl-methanol.

4-Allyloxy-2,3,5-trimethyl-pyridine N-oxide(4.0 g, 0.021 mol) was added dropwise under stirring to acetic anhydride (8.0 ml, 0.062 mol) preheated to 80° C., giving a final temperature of 120° C. The mixture was then heated at 80° C. for 1 hour. Methanol (15.0 ml) was added and the mixture was kept at 80° C. for 15 min. The volatiles were evaporated under reduced pressure. 10% HCl (20 ml) was added and the mixture was heated at 90° C. for 1 hour and then cooled to room temperature. Excess 2M NaOH was added and the mixture was extracted with $CH_2Cl_2$. The organic phase was separated out and dried. Volatiles were evaporated off giving the desired product as an oil (3.0 g, 75%), NMR: δ($COCl_3$) 2.1(s,3H), 2.25(s,3H), 4.4(m,2H), 4.65(s,2H), 4.75(s,1H), 5.2–5.65(m,2H), 5.9–6.45(m,1H), 8.3(s,1H).

Example 14. Method D. Preparation of 4-allyloxy-3,5-dimethyl-2-pyridinyl-methyl chloride hydrochloride.

Thionyl chloride (4.8 ml) dissolved in $CH_2Cl_2$ (12 ml) was added dropwise to a stirred solution of 4-allyloxy-3,5--dimethyl-2-pyridinylmethanol (8.0 g, 0.041 mol) in $CH_2Cl_2$ (80 ml), maintaining the temperature below 6° C. Then the mixture was stirred at room temperature for 45 min (final temperature 15° C.). Isopropanol (2 ml) was added and the solution was heated shortly at 35° C. The solvent was evaporated off and the crystalline residue was recrystallized from ethanol/ether giving the desired product (3.0 g, 29%), m.p. 115° C.

TABLE 3a

Intermediates. Summary of working examples.

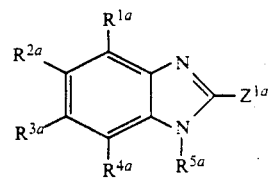

| No. | $Z^{1a}$ | $R^{1a}$ | $R^{2a}$ | $R^{3a}$ | $R^{4a}$ | $R^{5a}$ | Method$^x$ (Ex. No.) | Yield (%) | Mp (°C.), other data |
|---|---|---|---|---|---|---|---|---|---|
| I5 | SH | $CH_3$ | $CH_3$ | $CH_3$ | $CH_3$ | H | A(Ex I1) | 19 | NMR |
| I6 | SH | $CH_3$ | $CH_3$ | $CH_3$ | H | H | A(Ex I1) | 66 | NMR |
| I1 | SH | $CH_3$ | $CH_3$ | H | $CH_3$ | H | A(Ex I1) | 66 | NMR |
| I7 | SH | H | ⟨cyclohexyl⟩ | H | H | H | A(Ex I1) | 71 | NMR |
| I8 | SH | $CH_3$ | $OCH_3$ | $CH_3$ | H | H | A(Ex I1) | 78 | NMR |
| I9 | SH | $CH_3$ | $OCH_2CH_2OCH_3$ | $CH_3$ | H | H | A(Ex I1) | 85 | NMR |
| I10 | SH | $CH_3$ | $C_2H_5$ | $CH_3$ | H | H | A(Ex I1) | 89 | NMR |
| I11 | SH | H | $OCH_2CH_2CH_2O$—⟨phenyl⟩ | H | H | H | A(Ex I1) | 14 | 167 |
| I12 | SH | $CH_3$ | $O(CH_2)_6CH_3$ | $CH_3$ | H | H | A(Ex I1) | 73 | NMR |
| I2 | SH | $CH_3$ | $OCH_3$ | $CH_3$ | $CH_3$ | H | B(Ex I2) | 43 | NMR |
| I13 | SH | —CH=CH—CH=CH—CH$_2$CH$_2$— | | | H | H | A(Ex I1) | 23 | NMR |

$^x$Method A: The 1,2-phenylenediamine is reacted with $C_2H_5OCS_2K$
Method B: The 1,2-phenylenediamine is reacted with $CSCl_2$ TABLE 3b Intermediates. Summary of working examples.

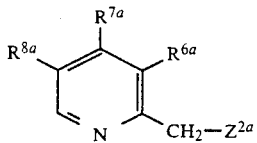

| No. | $Z^{2a}$ | $R^{6a}$ | $R^{7a}$ | $R^{8a}$ | Salt/Base | Method[xx] (Ex. No.) | Yield (%) | Mp (°C.) other data |
|---|---|---|---|---|---|---|---|---|
| I3 | OH | $CH_3$ | $OCH_2CH=CH_2$ | $CH_3$ | Base | C(Ex I3) | 75 | NMR |
| I4 | Cl | $CH_3$ | $OCH_2CH=CH_2$ | $CH_3$ | HCl | D(Ex I4) | 29 | 115° |
| I14 | OH | $CH_3$ | $OCH_2C\equiv CH$ | $CH_3$ | Base | C(Ex I3) | 88 | 70° |
| I15 | Cl | $CH_3$ | $OCH_2C\equiv CH$ | $CH_3$ | HCl | D(Ex I4) | 76 | 135° |
| I16 | OH | H | $-(CH_2)_4-$ | | Base | C(Ex I3) | 35 | NMR |
| I17 | Cl | H | $-(CH_2)_4-$ | | HCl | D(Ex I4) | 72 | NMR |
| I18 | OH | $CH_3$ | $OCH_2CH_2CH(CH_3)_2$ | $CH_3$ | Base | C(Ex I3) | 51 | NMR |
| I19 | Cl | $CH_3$ | $OCH_2CH_2CH(CH_3)_2$ | $CH_3$ | HCl | D(Ex I4) | 95 | |
| I20 | OH | $CH_3$ | $OCH_2$-tetrahydropyran | $CH_3$ | Base | C(Ex I3) | 30 | NMR |
| I21 | Cl | $CH_3$ | $OCH_2$-tetrahydropyran | $CH_3$ | HCl | D(Ex I4) | 82 | 133 |
| I22 | OH | $CH_3$ | $OC_2H_5$ | $CH_3$ | Base | C(Ex I3) | 70 | B.p. 120-26° C./0.4 mm |
| I23 | Cl | $CH_3$ | $OC_2H_5$ | $CH_3$ | HCl | D(Ex I4) | 89 | 157 |
| I24 | OH | $-CH=CH-O-$ | | H | Base | C(Ex I3) | 18 | $^1$H NMR |
| I25 | Cl | $-CH=CH-O-$ | | H | HCl | D(Ex I4) | 95 | 195 |

[xx]Method C: Rearrangement of the pyridine N-oxide with $(CH_3CO)_2O$.
Method D: Chlorination with $SOCl_2$.

NMR-data of the compounds in Table 3a and Table 3b

| Example No. | NMR-data: δ(ppm) |
|---|---|
| I5 | δ(DMSO-$d_6$) 2.05(s,6H), 2.2(s,6H). |
| I6 | δ(CDCl$_3$) 2.05(s,3H), 2.15(s,3H), 2.2(s,3H), 3.2(s,2H), 6.7(s,1H). |
| I1 | δ(CDCl$_3$) 2.0(s,3H), 2.05(s,3H), 2.1(s,3H), 3.3(br.s.,1H), 6.5(s,1H). |
| I7 | δ(DMSO-$d_6$) 1.1-2.05(m,10H), 2.4(m,1H), 6.85-7.05(m,3H). |
| I8 | δ(DMSO-$d_6$) 1.95(s,3H), 2.0(s,3H), 3.35(s,3H), 6.55(s,1H). |
| I9 | δ(CDCl$_3$) 2.1(s,3H), 2.15(s,3H), 3.2(s,3H), 3.35-3.8(m,4H), 6.6(s,1H). |
| I10 | δ(CDCl$_3$ + DMSO-$d_6$) 1.05(t,3H), 2.3(s,3H), 2.35(s,3H), 2.6(q,2H), 6.85(s,1H). |
| I12 | δ(CDCl$_3$) 0.5-1.7(m,13H), 2.0(s,3H), 2.1(s,3H), 3.15(s,2H), 3.35-3.6(m,2H), 6.6(s,1H). |
| I2 | δ(CDCl$_3$) 2.5(s,3H), 2.65(s,6H), 3.65(s,3H), 12.0(br.s.,1H). |
| I13 | δ(CDCL$_3$) 3.35(s,2H), 3.4(s,2H), 7.15-8.05(m,4H), 12.65(br.s.,1H), 13.3(br.s.,1H). |
| I3 | δ(CDCl$_3$) 2.1(s,3H), 2.25(s,3H), 4.4(m,2H), 4.65(s,2H), 4.75(s,1H), 5.2-5.65(m,2H), 5.9-6.45(m,1H), 8.3(s,1H). |
| I16 | δ(CDCl$_3$) 1.5-1.9(m,4H), 2.5-2.8(m,4H), 4.7(s,2H), 7.3(s,1H), 8.2(s,1H). |
| I17 | |
| I18 | δ(CDCl$_3$) 1.0(s,3H), 1.05(s,3H), 1.5-2.05(m,3H), 2.15(s,3H), 2.3(s,3H), 3.75-4.0(t,2H), 4.15-4.5(br.s.,1H), 4.65(s,2H), 8.3(s,1H). |
| I20 | δ(CDCl$_3$) 1.7-2.2(m,4H), 2.15(s,3H), 2.25(s,3H), 3.75-4.05(m,4H), 4.15-4.4(m,1H), 4.6(s,2H), 8.25(s,1H). |
| I24 | δ(CDCl$_3$) 8.55(d,1H), 7.8(d,1H), 7.5(d,1H), 7.0(d,1H), 5.1(s,2H) |

Pharmaceutical preparations containing a compound of the invention as active ingredient are illustrated in the following examples.

EXAMPLE 167

Syrup

A syrup containing 1% (weight per volume) of active substance was prepared from the following ingredients:

| | |
|---|---|
| 4,6-Dimethyl-5-ethyl-2-[[(4-methoxy-3,5-dimethyl-2-pyridinyl)methyl]thio]-1H-benzimidazole.HCl | 1.0 g |
| Sugar, powder | 30.0 g |
| Saccharine | 0.6 g |
| Glycerol | 5.0 g |
| Flavouring agent | 0.05 g |
| Ethanol 96% | 5.0 g |
| Distilled water q.s. to a final volume of | 100 ml |

Sugar and saccharine were dissolved in 60 g of warm water. After cooling the acid addition salt was dissolved in the sugar solution and glycerol and a solution of flavouring agents dissolved in ethanol were added. The mixture was diluted with water to a final volume of 100 ml.

The above given active substance may be replaced with other pharmaceutically acceptable acid addition salts.

EXAMPLE 168

Enteric-coated tablets

An enteric-coated tablet containing 20 mg of active compound was prepared from the following ingredients:

| I | |
|---|---|
| 5,6-Methylenedioxy-2-[[(4-methoxy-3,5-dimethyl--2-pyridinyl)methyl]sulfinyl]-1H-benzimidazole | 200 g |
| Lactose | 700 g |
| Methyl cellulose | 6 g |
| Polyvinylpyrrolidone cross-linked | 50 g |
| Magnesium stearate | 15 g |
| Sodium carbonate | 6 g |
| Distilled water | q.s. |
| II | |
| Cellulose acetate phthalate | 200 g |
| Cetyl alcohol | 15 g |
| Isopropanol | 2000 g |
| Methylene chloride | 2000 g |

I. 5,6-Methylenedioxy-2-[[(4-methoxy-3,5-dimethyl-2-pyridinyl)methyl]sulfinyl]-1H-benzimidazole, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10,000 tablets), each tablet containing 20 mg of active substance, in a tabletting machine using 6 mm diameter punches.

II. A solution of cellulose acetate phthalate and cetyl alcohol in isopropanol/methylene chloride was sprayed onto the tablets I in an Accela Cota ®, Manesty coating equipment. A final tablet weight of 110 mg was obtained.

EXAMPLE 169

Solution for intravenous administration

A parenteral formulation for intravenous use, containing 4 mg of active compound per ml, was prepared from the following ingredients:

| 4,6-Dimethyl-5-ethyl-2-[[(4-methoxy-3,5-dimethyl--2-pyridinyl)methyl]thio]-1H-benzimidazole | 4 g |
|---|---|
| Polyethylene glycol 400 for injection | 400 g |
| Disodium hydrogen phosphate | q.s. |
| Sterile water to a final volume of | 1000 ml |

4,6-Dimethyl-5-ethyl-2-[[(4-methoxy-3,5-dimethyl-2-pyridinyl)methyl]thio]-1H-benzimidazole was dissolved in polyethylene glycol 400 and 550 ml of water was added. pH of the solution was brought to pH 7.4 by adding a water solution of disodium hydrogen phosphate and water was added to a final volume of 1000 ml. The solution was filtered through a 0.22 μm filter and immediately dispensed into 10 ml sterile ampoules. The ampoules were sealed.

BIOLOGICAL TESTS

I. Inhibiting effect in vitro on acid secretion in isolated rabbit gastric glands

Test Method

Gastric gland preparation

Isolated rabbit gastric glands were prepared as described by Berglindh et al., Acta physiol. scand. 1976. 96. 150–159. This method involves vascular perfusion of the rabbit stomach via the gastric arteries, scraping and scissor mincing of the separated gastric mucosa and collagenase (0.1%, Type I, Sigma Chemicals, St. Louis, MO. USA) digestion at 37° C. for 60–90 min. The glands are then harvested and filtered through nylon cloth to remove coarse fragments. The glands are thereafter incubated at 37° C. in a medium containing NaCl 132.4 mM, KCl 5.4 mM, $NaH_2PO_4$ 5.0 mM, $NaH_2PO_4$ 1.0 mM, $MgSO_4$ 1.2 mM, $CaCl_2$ 1.0 mM, glucose 10 mM, and 1 mg/ml rabbit albumine, pH 7.4.

Measurement of acid secretion

The acid secretion in the isolated gland preparation was recorded by measuring the uptake of $^{14}C$-labelled aminopyrine into the glands as described by Berglindh et al., Acta physiol. scand. 1976. 97. 401–414. Accumulation of aminopyrine in the glands indicates gastric acid secretion within the glands. The standard medium contained $10^{-6}M$ $^{14}C$-aminopyrine (Amersham, Great Britain). After the incubation period, the glands were centrifuged, the supernatant was removed and the glands dried, weighed and dissolved in Soluene -350 (Packard, IU. USA). Samples of the supernatant and glands were separately counted in a scintillation counter. The accumulation of $^{14}C$-labelled aminopyrine in the glands was calculated as detailed by Berglindh et al., Acta physiol. scand. 1976. 97. 403.

Experimental protocol

Glands were incubated for 60 min. in the presence of $5 \times 10^{-5}M$ histamine and the test compound to be studied. The free base of the test compound was dissolved in methanol. The final concentration of methanol was 1% in the incubation medium, having no influence on the aminopyrine accumulation ratio. For each test compound a complete dose-response curve was generated by testing doses in duplicate in the concentration range $10^{-7}M$ to $10^{-4}M$. The logarithm of the concentration (in M) of the test compounds giving 50% inhibition of the aminopyrine accumulation in the glands ($IC_{50}$) is listed in Table 4 below.

II. Inhibiting effect in vivo on gastric acid secretion in conscious dog

Test Method

Chronic gastric fistula dogs were used. These dogs have been surgically provided with a gastric cannula in the stomach and a duodenal fistula used for direct intraduodenal administration of test compounds. Following a 4 weeks' recovery period after surgery, tests were performed once a week on each dog. Food and water were withdrawn 18 hours before each test.

Gastric acid secretion was induced by continuous infusion of histamine at individual doses (100–300 nmol/kg,h), resulting in submaximal secretion of gastric acid. At least 2 hours after onset of stimulation, when the gastric acid secretion had reached a steady level, the test compounds in the form of free base suspended in 0.5% Methocel ® (90 HG, 15.000, Dow Chem. Corp.), were given intraduodenally at doses from 1 to 8 μmol/kg. The gastric juice was collected by free flow from the gastric cannula in consecutive 30 minutes samples for 3 hours. The samples were titrated to pH 7.0 with 0.1 M NaOH using a Radiometer automatic titrator and the acid output was calculated.

The percent inhibition of acid secretion was calculated by comparing in each dog the acid output in the tests to the acid output in control tests when only the vehicle was given. The peak inhibitory effect for each compound is given in Table 5 below.

TABLE 4

Biological effects in isolated rabbit gastric glands

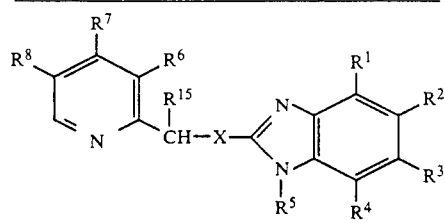

| No. | X | $R^{15}$ | $R^1$ | $R^2$ | $R^3$ | $R^4$ | $R^5$ | $R^6$ | $R^7$ | $R^8$ | -log IC$_{50}$ |
|---|---|---|---|---|---|---|---|---|---|---|---|
| 12 | SO | H | $CH_3$ | $CH_3$ | $CH_3$ | $CH_3$ | H | $CH_3$ | $OCH_3$ | $CH_3$ | 6.5 |
| 16 | SO | H | $CH_3$ | $CH_3$ | $CH_3$ | H | H | $CH_3$ | $OCH_3$ | $CH_3$ | 6.5 |
| 37 | SO | H | H | $OCH_3$ | H | H | H | H | —$(CH_2)_4$— | | 5.0 |
| 43 | SO | H | H | $OCH_2CN$ | H | H | H | $CH_3$ | $OCH_3$ | $CH_3$ | 4.4 |
| 51 | SO | H | H | $CH_2OH$ | $CH_3$ | H | H | $CH_3$ | $OCH_3$ | $CH_3$ | 6.1 |
| 104 | SO | H | H | $CH_2CH_2OCH_3$ | H | H | H | $CH_3$ | $OCH_3$ | $CH_3$ | 5.7 |
| 8 | SO | H | $CH_3$ | $OCH_3$ | $CH_3$ | H | H | $CH_3$ | $OCH_3$ | $CH_3$ | 6.5 |
| 1 | SO | H | $CH_3$ | $OCH_3$ | $CH_3$ | H | H | $CH_3$ | $CH_3$ | H | 6.7 |
| 58 | SO | H | $CH_3$ | $OCH_2CH_2OCH_3$ | $CH_3$ | H | H | $CH_3$ | $OCH_3$ | $CH_3$ | 5.9 |
| 60 | SO | H | $CH_3$ | $OCH_2CH_2OCH_3$ | $CH_3$ | H | H | H | $CH_3$ | $CH_3$ | 5.4 |
| 62 | SO | H | $CH_3$ | $COCH_3$ | $CH_3$ | H | H | $CH_3$ | $OCH_3$ | $CH_3$ | 6.2 |
| 64 | SO | H | $CH_3$ | $COCH_3$ | $CH_3$ | H | H | $CH_3$ | H | $CH_3$ | 5.8 |
| 66 | SO | H | $CH_3$ | $COC_2H_5$ | $CH_3$ | H | H | $CH_3$ | $OCH_3$ | $CH_3$ | 6.0 |
| 68 | SO | H | $CH_3$ | $C_2H_5$ | $CH_3$ | H | H | $CH_3$ | $OCH_3$ | $CH_3$ | 6.5 |
| 70 | SO | H | $CH_3$ | $C_2H_5$ | $CH_3$ | H | H | $CH_3$ | $OCH_3$ | H | 5.9 |
| 72 | SO | H | $C_2H_5$ | CN | $C_2H_5$ | H | H | $CH_3$ | $OCH_3$ | $CH_3$ | 5.0 |
| 74 | SO | H | $CH_3$ | $OCH_3$ | $CH_3$ | $CH_3$ | H | $CH_3$ | $OCH_3$ | $CH_3$ | 6.2 |
| 79 | SO | H | H | $\underset{CON}{\overset{CH_3}{\bigcirc}}$ | H | H | H | $CH_3$ | $OCH_3$ | $CH_3$ | 5.0 |
| 81 | SO | H | H | —$OCH_2O$— | | H | H | $CH_3$ | $OCH_3$ | $CH_3$ | 6.1 |
| 83 | SO | H | —CH=CH—CH=CH— | | | H | H | $CH_3$ | $OCH_3$ | $CH_3$ | 5.5 / 5.3 |
| 107 | SO | H | H | $OCH_3$ | H | H | $CO_2CH_3$ | $CH_3$ | $OCH_3$ | $CH_3$ | 5.8 |
| 108 | SO | H | H | H | $OCH_3$ | H | $CO_2CH_3$ | $CH_3$ | $OCH_3$ | $CH_3$ | |
| 10 | SO | H | $CH_3$ | $CH_3$ | $CH_3$ | $CH_3$ | H | $CH_3$ | $OCH_2CH=CH_2$ | $CH_3$ | 6.1 |
| 14 | SO | H | $CH_3$ | $CH_3$ | $CH_3$ | H | H | $CH_3$ | $OCH_2CH=CH_2$ | $CH_3$ | 6.1 |
| 18 | SO | H | $CH_3$ | $CH_3$ | H | $CH_3$ | H | $CH_3$ | $OCH_2CH=CH_2$ | $CH_3$ | 5.9 |
| 20 | SO | H | $CH_3$ | $CH_3$ | H | $CH_3$ | H | $CH_3$ | $OCH_3$ | $CH_3$ | 6.0 |
| 22 | SO | H | $CH_3$ | $CH_3$ | H | H | H | $CH_3$ | $OCH_2CH=CH_2$ | $CH_3$ | 6.0 |
| 24 | SO | H | H | $CH_3$ | $CH_3$ | H | H | $CH_3$ | $OCH_2CH=CH_2$ | $CH_3$ | 6.0 |
| 26 | SO | H | $CH_3$ | H | H | $CH_3$ | H | $CH_3$ | $OCH_2CH=CH_2$ | $CH_3$ | 5.9 |
| 28 | SO | H | $CH_3$ | H | H | H | H | $CH_3$ | $OCH_2CH=CH_2$ | $CH_3$ | 5.9 |
| 30 | SO | H | H | $CH_3$ | H | H | H | $CH_3$ | $OCH_2CH=CH_2$ | $CH_3$ | 5.9 |
| 32 | SO | H | H | $OCH_3$ | H | H | H | $CH_3$ | $OCH_2CH=CH_2$ | $CH_3$ | 5.6 |
| 34 | SO | H | H | $OCH_3$ | H | H | H | $CH_3$ | $OCH_2C≡CH$ | $CH_3$ | 5.0 |
| 35 | SO | H | H | $OCH_3$ | H | H | H | H | $OCH_3$ | $C_2H_5$ | 5.6 |
| 41 | SO | H | $CH_3$ | H | $CH_3$ | H | H | $CH_3$ | $OCH_2CH=CH_2$ | $CH_3$ | 5.9 |
| 45 | SO | H | H | $\underset{}{\bigcirc}$ (cyclohexyl) | H | H | H | $CH_3$ | $OCH_3$ | $CH_3$ | 6.1 |
| 55 | SO | H | H | $COOCH_3$ | $CH_3$ | H | H | $CH_3$ | $OCH_2CH=CH_2$ | $CH_3$ | 5.3 |
| 87 | SO | H | H | —$CH_2CH_2CH_2CH_2$— | | H | H | $CH_3$ | $OCH_3$ | $CH_3$ | 6.3 |
| 91 | SO | H | H | $OCH_2CH_2CH_2O$-phenyl | | H | H | $CH_3$ | $OCH_3$ | $CH_3$ | 5.8 |
| 2 | SO | H | $CH_3$ | $O(CH_2)_6CH_3$ | $CH_3$ | H | H | $CH_3$ | $OCH_3$ | $CH_3$ | 5.9 |
| 94 | SO | H | H | $C_2H_5$ | H | H | H | $CH_3$ | $OCH_2CH=CH_2$ | $CH_3$ | 6.6 |
| 96 | SO | H | H | $OCH_3$ | H | H | H | $CH_3$ | $OCH_2CH_2CH(CH_3)_2$ | $CH_3$ | 6.1 |
| 98 | SO | H | —CH=CH—CH=CCH$_2$CH$_2$— | | | H | H | $CH_3$ | $OCH_3$ | $CH_3$ | 5.6 |

TABLE 4-continued

Biological effects in isolated rabbit gastric glands

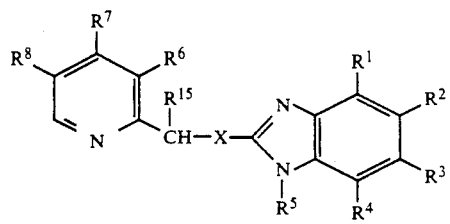

| No. | X | $R^{15}$ | $R^1$ | $R^2$ | $R^3$ | $R^4$ | $R^5$ | $R^6$ | $R^7$ | $R^8$ | -log IC$_{50}$ |
|---|---|---|---|---|---|---|---|---|---|---|---|
| 102 | SO | H | H | C(CH$_3$)$_3$ | H | H | H | CH$_3$ | OCH$_2$CH=CH$_2$ | CH$_3$ | 5.9 |
| 104 | SO | H | H | CH$_2$CH$_2$OCH$_3$ | H | H | H | CH$_3$ | OCH$_3$ | CH$_3$ | 5.7 |
| 106 | SO | H | H | ![cyclohexane dioxy] | H | H | H | CH$_3$ | OCH$_3$ | CH$_3$ | 6.0 |
| 111 | SO | H | H | CH(CH$_3$)$_2$ | H | H | H | CH$_3$ | OCH$_2$-(tetrahydrofuran) | CH$_3$ | 6.2 |
| 113 | SO | H | H | CH$_2$CH$_2$COCH$_3$ | H | H | H | CH$_3$ | OCH$_2$CH=CH$_2$ | CH$_3$ | 5.8 |
| 118 | SO | H | H | O-phenyl | H | H | H | CH$_3$ | OCH$_3$ | CH$_3$ | 6.4 |
| 120 | SO | H | H | OCH$_2$CH$_2$-phenyl | H | H | H | CH$_3$ | OCH$_3$ | CH$_3$ | 6.3 |
| 124 | SO | H | H | phenyl | H | H | H | CH$_3$ | OCH$_3$ | CH$_3$ | 7.0 |
| 129 | SO | H | H | Br | H | H | H | CH$_3$ | OCH$_2$CH=CH$_2$ | CH$_3$ | 6.0 |
| 142 | SO | H | H | —OCH$_2$O— | | H | H | CH$_3$ | CH$_3$ | CH$_3$ | 6.0 |
| 143 | SO | H | H | C(=O)OCH$_3$ | CH$_3$ | H | H | H | OCH$_3$ | C$_2$H$_5$ | 6.1 |
| 145 | SO | H | CH$_3$ | CH$_3$ | CH$_3$ | H | H | CH$_3$ | CH$_3$ | H | 6.2 |
| 147 | SO | H | CH$_3$ | CH$_3$ | CH$_3$ | H | H | H | CH$_3$ | CH$_3$ | 6.4 |
| 149 | SO | H | CH$_3$ | CH$_3$ | CH$_3$ | H | H | CH$_3$ | H | CH$_3$ | 6.2 |
| 151 | SO | H | CH$_3$ | CH$_3$ | H | CH$_3$ | H | CH$_3$ | CH$_3$ | H | 6.3 |
| 153 | SO | H | CH$_3$ | CN | CH$_3$ | H | H | CH$_3$ | OC$_2$H$_5$ | CH$_3$ | 5.2 |
| 77 | SO | H | H | CH$_3$ | CH$_3$ | H | H | H | OCH$_3$ | C$_2$H$_5$ | 6.0 |
| 159 | SO | H | H | CF$_3$ | H | H | H | CH$_3$ | OCH$_2$-(tetrahydrofuran) | CH$_3$ | 6.3 |

TABLE 5
Biological effects in conscious dogs

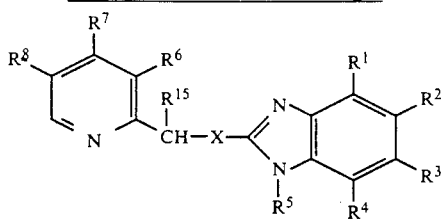

| No. | X | $R^{15}$ | $R^1$ | $R^2$ | $R^3$ | $R^4$ | $R^5$ | $R^6$ | $R^7$ | $R^8$ | (I.D.) DOSE (μmol/kg) | % INHIB |
|---|---|---|---|---|---|---|---|---|---|---|---|---|
| 84 | S | H | H | —CH=CH—CH=CH— | | H | H | $CH_3$ | $OCH_3$ | $CH_3$ | 8 | 85 |
| 109 | S | H | H | $SCH_3$ | H | H | H | $CH_3$ | $OCH_3$ | $CH_3$ | 8 | 60 |

Comment to the test results

It is seen in Table 4 and Table 5 that the tested compounds potently inhibited gastric acid secretion both in vitro and in vivo.

What we claim is:

1. A compound of the formula

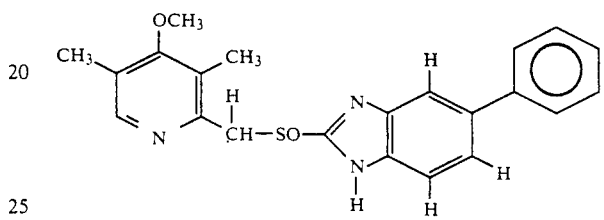

* * * * *